US010588695B2

(12) United States Patent
Walsh et al.

(10) Patent No.: US 10,588,695 B2
(45) Date of Patent: Mar. 17, 2020

(54) CATHETER DEVICE FOR TRANSMITTING AND REFLECTING LIGHT

(71) Applicants: President and Fellows of Harvard College, Cambridge, MA (US); The Brigham and Women's Hospital, Boston, MA (US); Children's Medical Center Corporation, Boston, MA (US); Massachusetts Institute of Technology, Cambridge, MA (US)

(72) Inventors: Conor J. Walsh, Cambridge, MA (US); Ellen T. Roche, Cambridge, MA (US); Panagiotis Polygerinos, Somerville, MA (US); Lucia R. Schuster, Munich (DE); Jeffrey Michael Karp, Brookline, MA (US); Yuhan Lee, Cambridge, MA (US); Pedro J. del Nido, Lexington, MA (US); Assunta Fabozzo, Jamaica Plain, MA (US); Ingeborg Friehs, Newton, MA (US); Steven Charles Wasserman, Concord, MA (US)

(73) Assignees: President and Fellows of Harvard College, Cambridge, MA (US); The Brigham and Women's Hospital, Boston, MA (US); Children's Medical Center Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 490 days.

(21) Appl. No.: 15/310,877

(22) PCT Filed: May 13, 2015

(86) PCT No.: PCT/US2015/030567
§ 371 (c)(1),
(2) Date: Nov. 14, 2016

(87) PCT Pub. No.: WO2015/175662
PCT Pub. Date: Nov. 19, 2015

(65) Prior Publication Data
US 2017/0079717 A1  Mar. 23, 2017

Related U.S. Application Data

(60) Provisional application No. 61/996,832, filed on May 14, 2014.

(51) Int. Cl.
*A61B 18/24* (2006.01)
*A61M 25/00* (2006.01)
(Continued)

(52) U.S. Cl.
CPC ......... *A61B 18/24* (2013.01); *A61M 25/0067* (2013.01); *A61B 2018/0022* (2013.01);
(Continued)

(58) Field of Classification Search
CPC ............ A61B 18/24; A61B 2018/0022; A61B 2018/0025; A61B 2018/00255;
(Continued)

(56) References Cited

U.S. PATENT DOCUMENTS

| 7,918,800 | B1* | 4/2011 | Brown | A61B 5/061 |
| | | | | 600/300 |
| 2003/0050632 | A1* | 3/2003 | Fjield | A61B 17/2202 |
| | | | | 606/27 |

(Continued)

FOREIGN PATENT DOCUMENTS

| EP | 812573 A2 | 12/1997 |
| EP | 821916 A2 | 2/1998 |

OTHER PUBLICATIONS

E. Roche, et al., "A light-reflecting balloon catheter for atraumatic tissue defect repair," 7 Science Translational Medicine 306ra149 (Sep. 23, 2015).
(Continued)

*Primary Examiner* — Robert A Lynch
(74) *Attorney, Agent, or Firm* — Modern Times Legal; Robert J. Sayre

(57) ABSTRACT

An insertable light-dispensing catheter device, comprising a shaft including a proximal and distal end, a light guide extending through the shaft, and a mirror displaceably extendable from the catheter into a position where the mirror
(Continued)

receives and reflects light emitted from the light guide. The mirror can be in the form of a coating on an inflatable balloon; and the balloon, when inflated, can press a patch against a defect (e.g., a ventricular septical defect), while the light cures an adhesive that binds the patch to the structure with the defect, thereby remedying the defect.

21 Claims, 18 Drawing Sheets

(51) Int. Cl.
    *A61B 18/00*     (2006.01)
    *A61B 18/22*     (2006.01)

(52) U.S. Cl.
    CPC ............... *A61B 2018/00285* (2013.01); *A61B 2018/00351* (2013.01); *A61B 2018/00494* (2013.01); *A61B 2018/00982* (2013.01); *A61B 2018/2272* (2013.01)

(58) Field of Classification Search
    CPC ........... A61B 2018/00285; A61B 2018/00351; A61B 2018/00982; A61B 2018/2261; A61B 2018/2272; A61B 17/00491; A61B 17/005; A61B 17/0057; A61B 17/0061; A61B 17/00615; A61B 17/00623; A61B 17/0065; A61B 17/12013; A61B 1/00082; A61B 1/00101; A61B 1/00163; A61B 1/00165; A61B 1/00174; A61B 1/00183; A61M 25/0067
See application file for complete search history.

(56) References Cited

U.S. PATENT DOCUMENTS

| | | | | |
|---|---|---|---|---|
| 2005/0192626 A1* | 9/2005 | Widomski | ......... | A61B 17/0057 606/213 |
| 2011/0293667 A1* | 12/2011 | Baksh | .................. | C12N 5/0663 424/400 |
| 2012/0010644 A1* | 1/2012 | Sideris | ............... | A61B 17/0057 606/192 |
| 2013/0237929 A1* | 9/2013 | Hong | .................. | A61B 17/0057 604/264 |
| 2014/0275770 A1* | 9/2014 | Gunday | ............. | A61B 1/00154 600/104 |
| 2015/0025531 A1* | 1/2015 | Gittard | ............... | A61B 18/1492 606/41 |

OTHER PUBLICATIONS

N. Lang, et al., "A Blood-Resistant Surgical Glue for Minimally Invasive Repair of Vessels and Heart Defects," 6 Science Translational Medicine 218ra6 (Jan. 8, 2014).

A. Dodge-Khatami, et al., "Spontaneous Closure of Small Residual Ventricular Septal Defects After Surgical Repair," 83 Ann Thorac Surg 902-06 (2007).

European Patent Office, Extended European Search Report for EP App. No. 15792211.3 (dated Mar. 5, 2018).

\* cited by examiner

Insertion at 18.5 mm

Insertion at 10 mm

Insertion at 0 mm

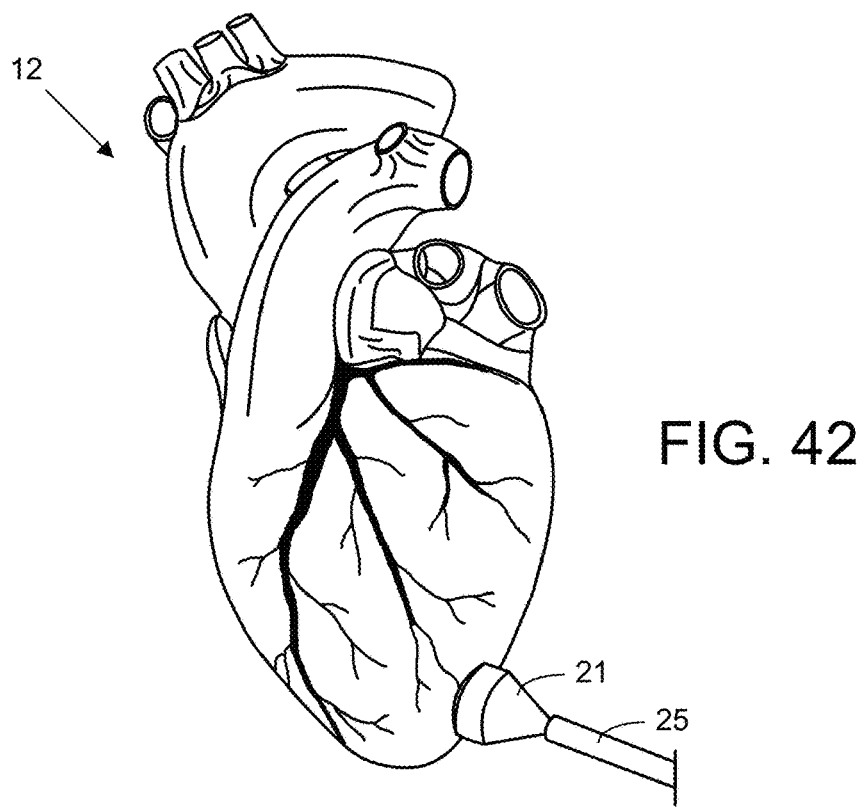
FIG. 42
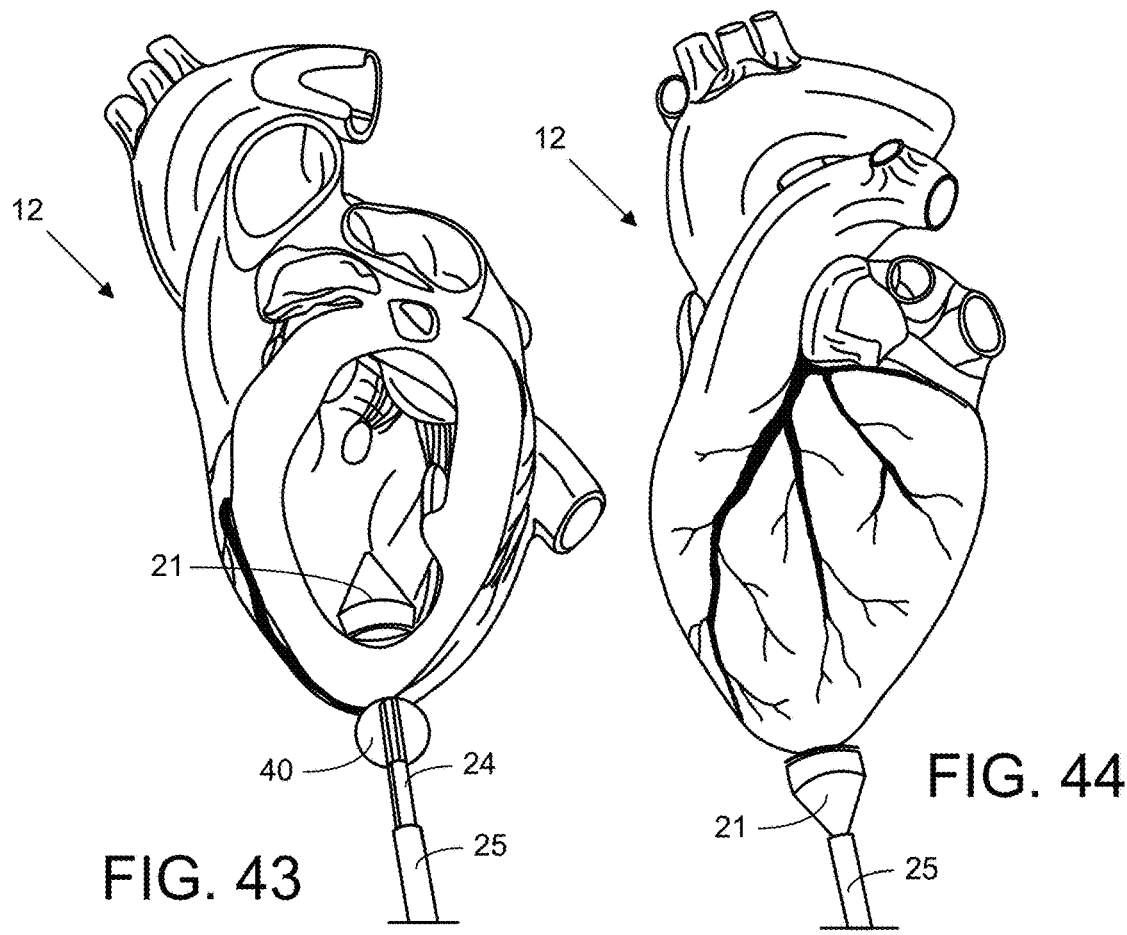
FIG. 43
FIG. 44

CATHETER DEVICE FOR TRANSMITTING AND REFLECTING LIGHT

GOVERNMENT SUPPORT

This invention was made with government support under Grant No. GM 086433 awarded by the National Institute of Health. The United States Government has certain rights in the invention.

BACKGROUND

A ventricular septal defect (VSD) is an abnormal communication between the right and the left ventricle of the heart in the form of a hole in the septum, which can lead to ventricular dysfunction and pulmonary hypertension. Illustrations comparing a normal heart septum with a heart that suffers from a ventricular septal defect are provided in FIGS. 1 and 2. The ventricular septal defect is the most common congenital cardiac defect and cause of death in infants under one year.

Current therapies for closure of ventricular septal defects have inherent limitations. Surgical techniques are invasive and require cardiopulmonary bypass [K. G. Shann, "Complications relating to perfusion and extracorporeal circulation associated with the treatment of patients with congenital heart disease: consensus definitions form the Multi-societal Database Committee for Pediatric and Congenital Heart Disease," 18 Cardiol. Young 206-214 (2008)]. In an effort to reduce the invasiveness of the procedure, catheter-based (percutaneous) interventions have become available but face major challenges due to limitations of delivery and securing devices inside the beating heart. Most percutaneous devices are composed of fragile metal frames and rely on mechanical means of gripping tissue which can cause injury to critical structures, such as heart valves, or the conduction system and tissue erosion (Shann).

SUMMARY

Apparatus and methods for transmitting light through a catheter device, particularly to cure an adhesive that secures a patch delivered through the catheter to repair a congenital, acquired, or iatrogenic tissue defect, such as a ventricular septal defect, are described herein, where various embodiments of the apparatus and methods may include some or all of the elements, features and steps described below.

Embodiments of the catheter device that transmit and change the direction of light while, optionally, simultaneously applying pressure to a biocompatible, photocurable adhesive from the opposite side of a defect in biological tissue, thereby closing or significantly reducing the size of the defect.

Embodiments of the catheter device represent an alternative to the currently available therapies for intra-cardiac septal defect closure (surgical and trans-catheter procedures), which are associated with early and late complications due to tissue damage from anchoring devices or sutures. These embodiments are based on a uniquely designed system for delivery of an ultraviolet (UV) light activated adhesive for attachment of a biodegradable patch on a balloon treated with UV-reflecting layer.

Although the device was originally designed for the closure of ventricular septal defects, the technology can easily be applied to the closure of other defects, or indeed for other applications as is detailed below.

Embodiments of the device and methods can provide numerous advantages and benefits, including the following.

First, the device can achieve patch-to-tissue adhesion by transmitting, reflecting and spreading UV light, with no mechanical anchoring and without leaving any permanent foreign material in the body. Second, the device can be designed to allow minimally invasive access to the defect site, even in extremely challenging, hard-to-access anatomical settings. The entire procedure can be easily visualized and monitored with 2D and 3D ultrasound or endoscopic guidance. Additionally, the device can quickly and consistently deploy and release the patch to rapidly achieve occlusion of a body defect opening with adhesion to internal tissue. Finally, the presence of a stabilizing balloon can ensure adequate compression forces to achieve adhesive activation. Although devices for closure of body defect openings have been previously proposed, most rely on mechanical or suture-based attachment, which can erode tissue over time. With this device, an elastic biodegradable adhesive can provide adequate tissue fixation, enduring cyclical and shear forces. The device is also amenable to growing tissues (for example, for implanting in the pediatric population), where permanent devices can be problematic. The device may remain in the body for less than five minutes without any long-term adverse device-related complications foreseen.

Additionally, components of the device that are left in the heart can be completely compliant/elastomeric and/or biodegradable. These characteristics can minimize local tissue damage (e.g., by substantially matching the elasticity of the tissue) and the amount of foreign materials left in the heart (and resultant foreign body response) and can act as a scaffold for tissue repopulation and septum self-healing. Accordingly, the device can be particularly advantageous for use on delicate and friable tissue.

Further, embodiments of the methods and apparatus described herein may omit any mechanical attachment of patch to septum (e.g., unlike most of the known prior art, there is no need for mechanical means of anchoring in the heart). Consequently, methods and apparatus described herein reduce risk of local tissue damage. Instead, an elastomeric patch and adhesive that are tailored to match the elasticity of the heart can be used.

Further still, advantages can be obtained from the use of a flexible, inflatable and non-stick substrate (e.g., a balloon) or deployable applicator can be used to apply pressure to a patch and adhesive while curing.

Moreover, the apparatus can have a smaller profile, making it more suitable for use on infants or young children (resulting in reduced problems/complications in infants and children), which is important, as a ventricular septal defect is preferably treated before the patient reaches one year of age. Importantly, use of the device is substantially less invasive and does not require open heart surgery or cardiopulmonary bypass to provide the patch. Rather, the apparatus and methods can be used to provide a patch in vivo on the septum of a beating heart.

Finally, a retrieval catheter shaft can extend from the stabilization/support balloon; and the balloon with the mirror can be removed through that catheter shaft after the patch is adhered to the internal tissue.

BRIEF DESCRIPTION OF THE DRAWINGS

FIG. 42 illustrates an application where an embodiment of the device is used for epicardial patch delivery.

FIGS. 43 and 44 illustrate use of an embodiment of the device for apical closure.

Figures 1, 2:
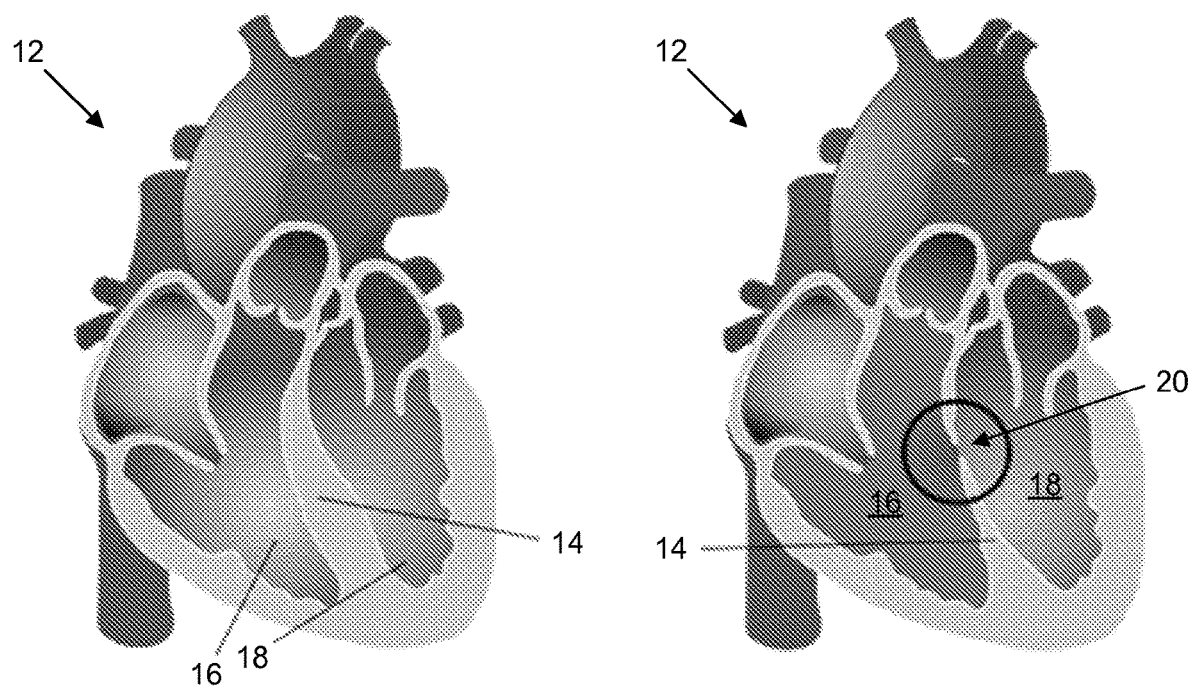
FIG. 1 is a sectional illustration of a normal heart 12 with a right ventricle 16 and a left ventricle 18
FIG. 2 is a sectional illustration of a heart 12 with a ventricular septal defect 20.
Figure 3:
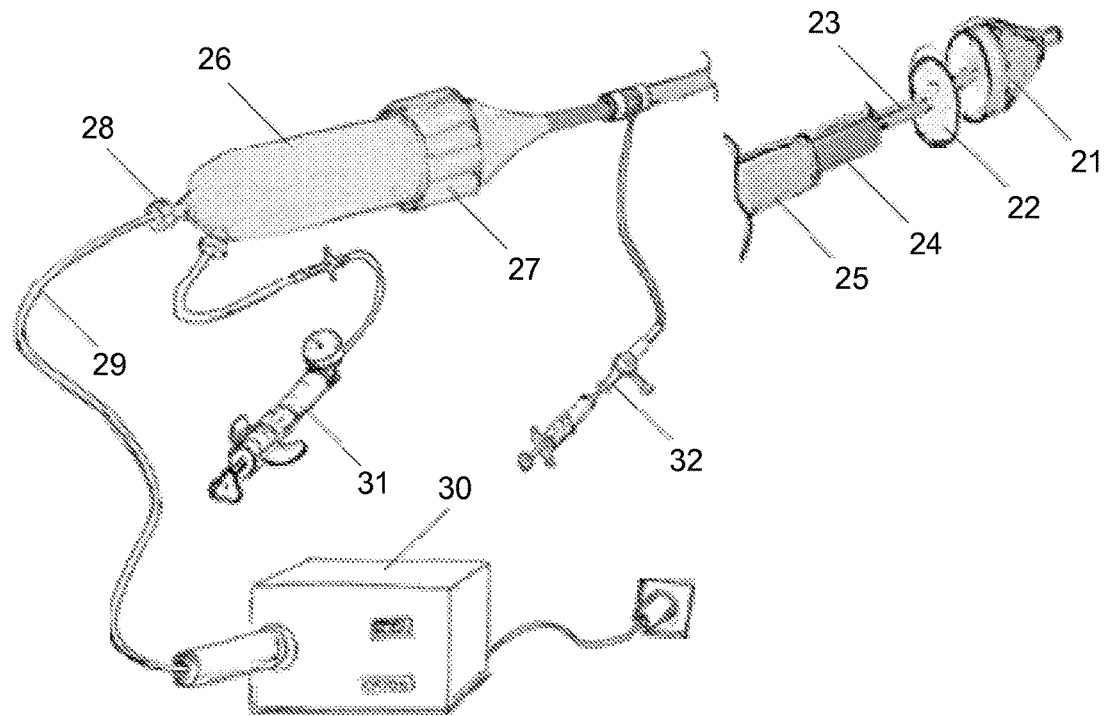
FIG. 3 is an illustration of an embodiment of a light-dispensing catheter device.

Additional embodiments of the apparatus and methods are shown and described in the pages that follow the numbered drawings.

In the accompanying drawings, like reference characters refer to the same or similar parts throughout the different views; and apostrophes are used to differentiate multiple instances of the same or similar items sharing the same reference numeral. The drawings are not necessarily to scale; instead, emphasis is placed upon illustrating particular principles in the exemplifications discussed below.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise herein defined, used or characterized, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances. Percentages or concentrations expressed herein can represent either by weight or by volume. Processes, procedures and phenomena described below can occur at ambient pressure (e.g., about 50-120 kPa—for example, about 90-110 kPa) and temperature (e.g., −20 to 50° C.—for example, about 10-35° C.) unless otherwise specified.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Additionally, the various components identified herein can be provided in an assembled and finished form; or some or all of the components can be packaged together and marketed as a kit with instructions (e.g., in written, video or audio form) for assembly and/or modification by a customer to produce a finished product.

Figure 5:
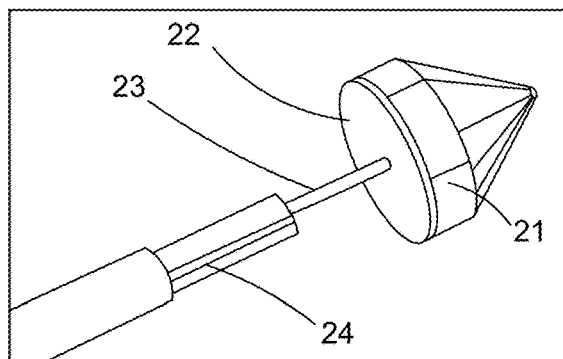
FIG. 5 is a magnified view of the extended catheter shafts 23, 24, and 25 with the balloon 21 and patch 22 of the device of FIG. 4.
Figure 4:
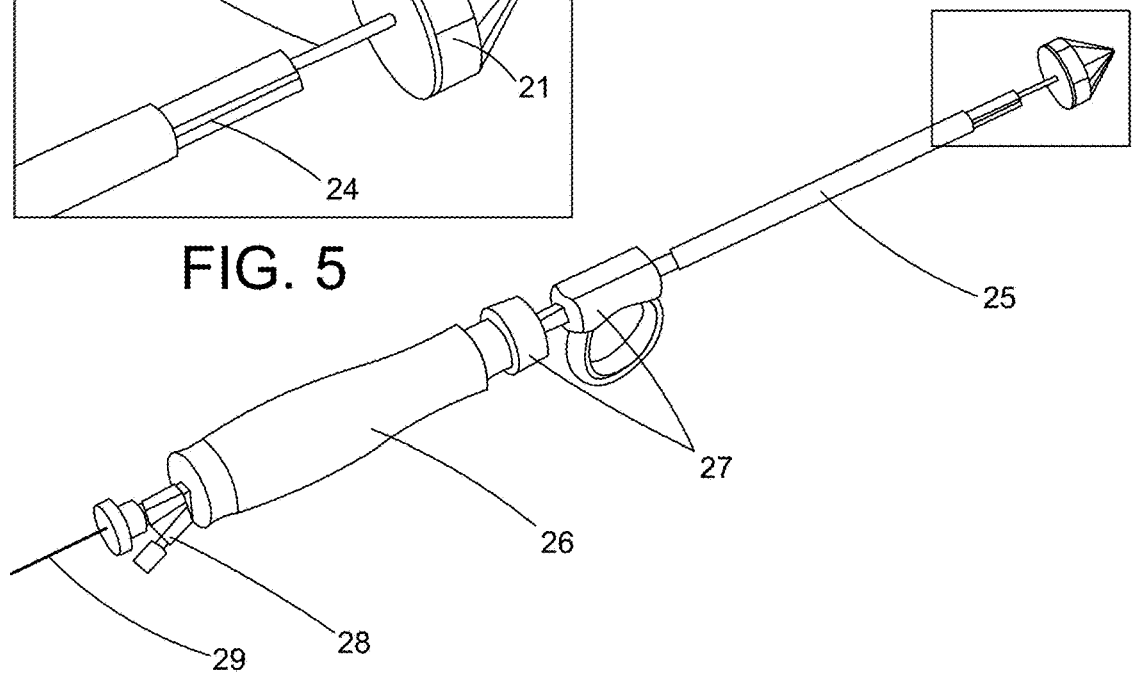
FIG. 4 is an illustration of another embodiment of a light-dispensing catheter device.

Structure of the Device:

Embodiments of the device, as shown in FIGS. 3-7, can include a distal balloon 21, a reflective coating (mirror) on the balloon 21, multiple shafts in the catheter, a light-activated adhesive 46, and a patch 22. In greater detail, FIG. 5 shows the following components: a balloon 21 with a plasma surface treatment and an aluminum-polyp-xylylene) coating, a poly-glycerol-sebacate urethane (PGSU) patch 22 with spread poly-glycerol-sebacate acrylate (PGSA) adhesive 46, an inner shaft 23 that incorporates the optical fiber 29 and saline and deploys the distal balloon 21 and patch 22, an intermediate single or multi-lumen shaft 24 that deploys the proximal balloon 40, an 18.0-20.0 F. introducer shaft 25, a handle 26, an inner-intermediate shaft coupling/decoupling mechanism in the form of a sliding mechanism 27, a Y-connector 28, an optical fiber optic 29 inserted through the Y-connector 28, a light source 30 (that produces, e.g., UV light), an inflation device 31, and a syringe 32.

Figure 6:
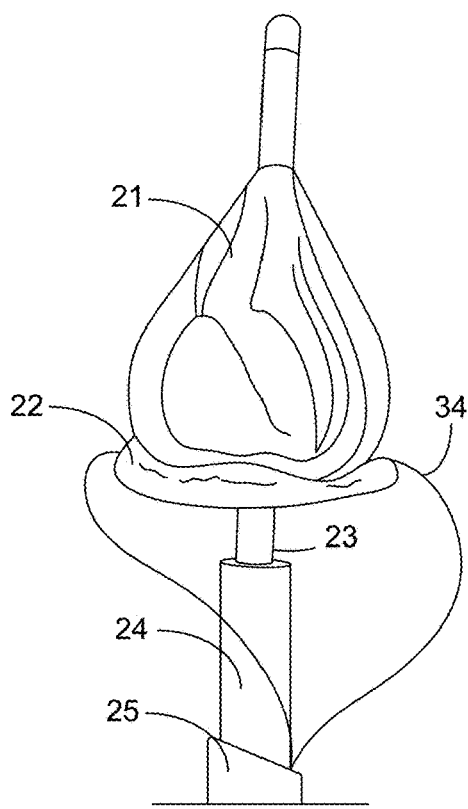
FIG. 6 is an image of an embodiment of an inflated metalized balloon 21 for use with the light-dispensing catheter device.
Figure 7:
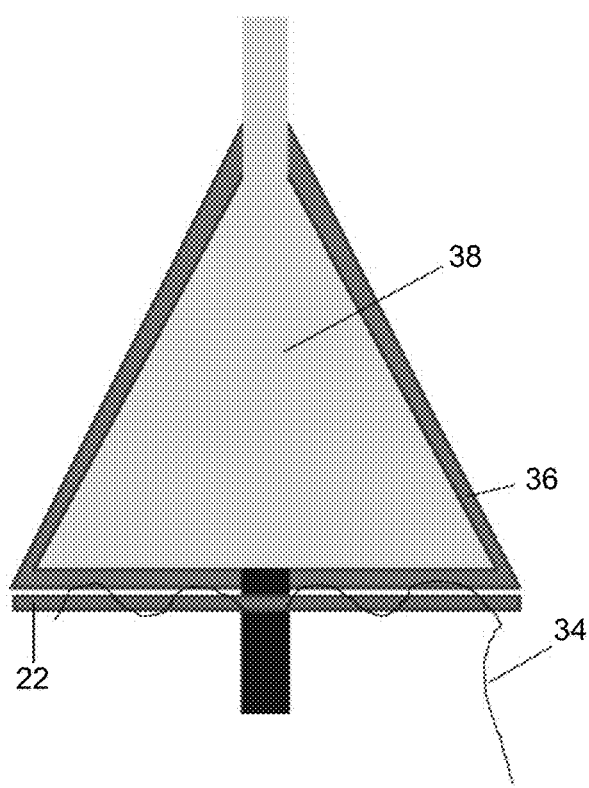
FIG. 7 is a schematic sectional illustration of the distal balloon 21, including an inner coated balloon 38 and an outer balloon 36, and patch 22 of FIG. 6.

The distal balloon 21, embodiments of which are shown in FIGS. 6 and 7, can be a medical balloon coated with a metallic and protective/omniphobic coating and can include two layers 36 and 38. The distal balloon 21 can accomplish the following three functions: (a) deploying the patch 22 through temporary sutures 34 attaching the patch 22 to an outer layer on the distal balloon 21 so that it deploys with the balloon 21 (b) applying a compressive force onto the patch 22 and stabilizing the patch 22 during the curing process, and (c) reflecting light to the septal surface exposing the adhesive 46 to light through the patch 22 for curing. The balloon 21 can be formed of, e.g., urethane, which can withstand high pressure, provide good conformance on the surface geometry (thereby preventing damage to the internal tissue), and transmit more than 20N of force to the patch 22 (for glue curing). In FIGS. 3-7, the distal balloon 21 has a conical shape, though the balloon 21 can take on other shapes. In particular embodiments, the balloon 21, itself, can be made of a bioabsorbable material; and the catheter can inflate the balloon 21, provide light for curing, and then detaches from the balloon 21, leaving the balloon 21 behind for closure of the ventricular septal defect 20.

The coating can be in the form of a multi-layer coating including a plasma surface treatment and a vapor deposited aluminum, polyp-xylylene) (e.g., Parylene-C) coating and/or an anti-thrombogenic coating. With plasma treatment, aluminum evaporation and optional poly(p-xylylene) coating, reflectance of greater than 90% has been achieved with the mirror coating. Because of its barrier properties, biocompatibility and chemical and biological inertness, poly(p-xylylene) can serve as a protective coating material for the reflective balloon 21. The poly(p-xylylene) deposition process does not influence the reflective coating reflectivity significantly.

In alternative embodiments, the mirror can be provided on/toward the distal tip of the light guide inserted into the distal balloon 21 (e.g., in a light-emitting shaft 23 inserted into the balloon 21 beyond the distal tip of an optical fiber 29 positioned within the shaft 23 and through which the light is delivered) to reflect and distribute the light back onto the patch 22.

In particular embodiments, the balloon 21 with the mirror can be contained in an outer balloon layer 36. A suture 34 can pass through the outer balloon layer 36 and through the patch 22 so that the patch 22 deploys with expansion of the balloon 21. An end of the suture 34 can be pulled outside the body through the outer shaft 25 to release the secured patch 22 from the outer layer of the balloon 21.

In other embodiments, the distal balloon can be replaced with a foldable/unfoldable sheet for delivering patch 22 and adhesive 46. In some embodiments, the adhesive 46 can be contained in the patch 22 and released when pressured by force from the inflated distal balloon 21.

The multiple shafts that form the catheter can include the following: (a) an outer shaft 25 for device insertion, securement to the right ventricle 16 and protection of inner components; (b) an intermediate shaft 24 that advances through the ventricular septal defect 20 with the distal balloon 21 and the patch 22 and that retracts to deploy the distal balloon 21 and patch 22 inside left ventricle 18; and (c) an inner shaft 23 that deploys the distal balloon 21 and protects the light guide on insertion. Relative movement of the shafts 23, 24, and 25 can be controlled by the handle 26, with locking mechanisms for the shafts 23, 24, and 25. The catheter, which can have an outer diameter of about 8 mm or less, can also include an injection lumen leading to the applicator tool on the septum 14.

The adhesive 46 can be in the form of a poly-glycerol-sebacate acrylate (PGSA) or alternative light-activated glue. A suitable form of PGSA is described in N. Lang, M. J.

Pereira, Y. Lee, I. Friehs, N. V. Vasilyev, E. N. Feins, K. Ablasser, E. D. O'Cearbhaill, C. Xu, A. Fabozzo, R. Padera, S. Wasserman, F. Freudenthal, L. S. Ferreira, R. Langer, J. M. Karp, P. J. del Nido, A Blood-Resistant Surgical Glue for Minimally Invasive Repair of Vessels and Heart Defects. Sci. Transl. Med. 6, 218ra6 (2014). The adhesive 46 is both biocompatible and biodegradable and is activated via exposure to light (e.g., ultraviolet light). In some embodiments, the adhesive 46 can be coated on the patch 22 before the device is inserted into the patient. In other embodiments, the adhesive 46 can be stored in reservoirs in the patch 22, where the reservoirs are sealed with removable absorbable/pressure-sensitive adhesive 46 that is released when pressure is applied by the expanding balloon 21. In other embodiments, the reservoirs can be sealed with valves. For non-photocurable adhesives 46, applying pressure may cause chambers to burst to release other type of adhesive (for example thermally curing adhesive or adhesive that cures on contact with water). In still other embodiments, the adhesive 46 can be injected through the catheter in vivo.

Figure 31:
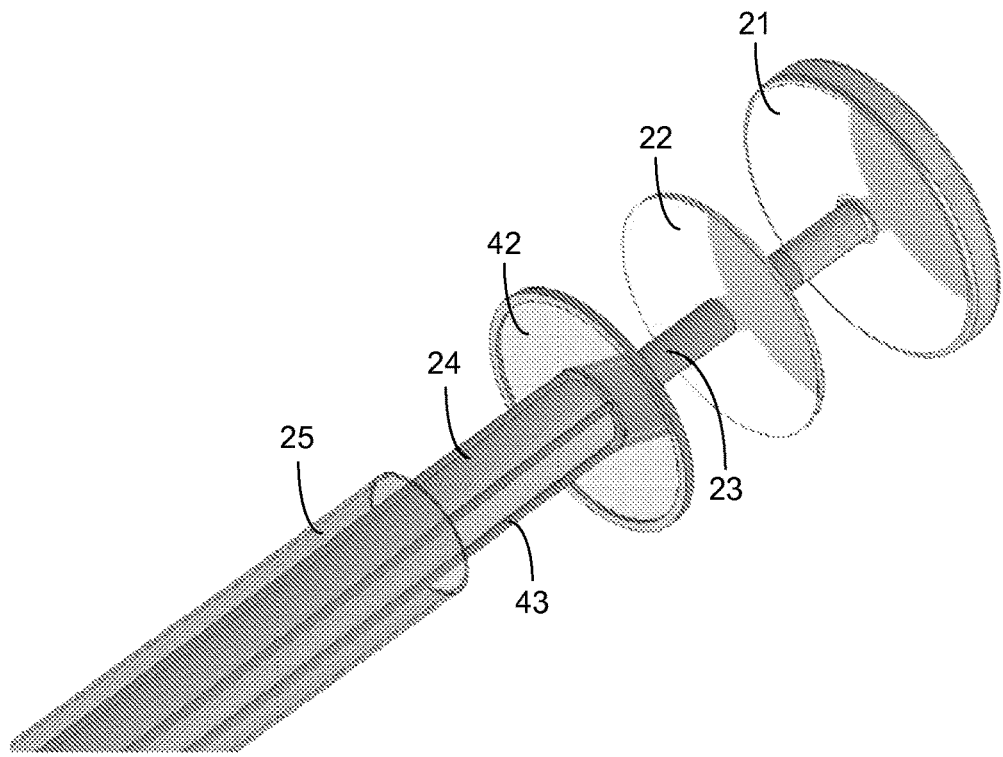
FIGS. 31-34 illustrate embodiments of a device that includes an adhesive delivery dispenser 42.
Figure 32:
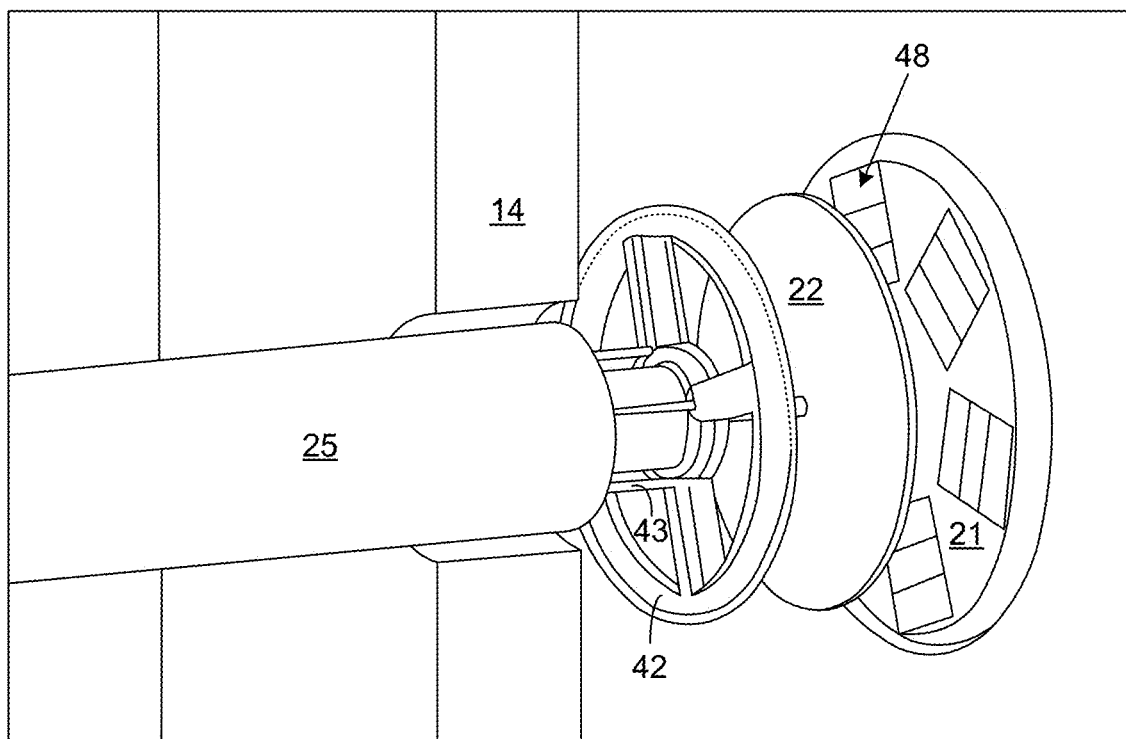
Figure 33:
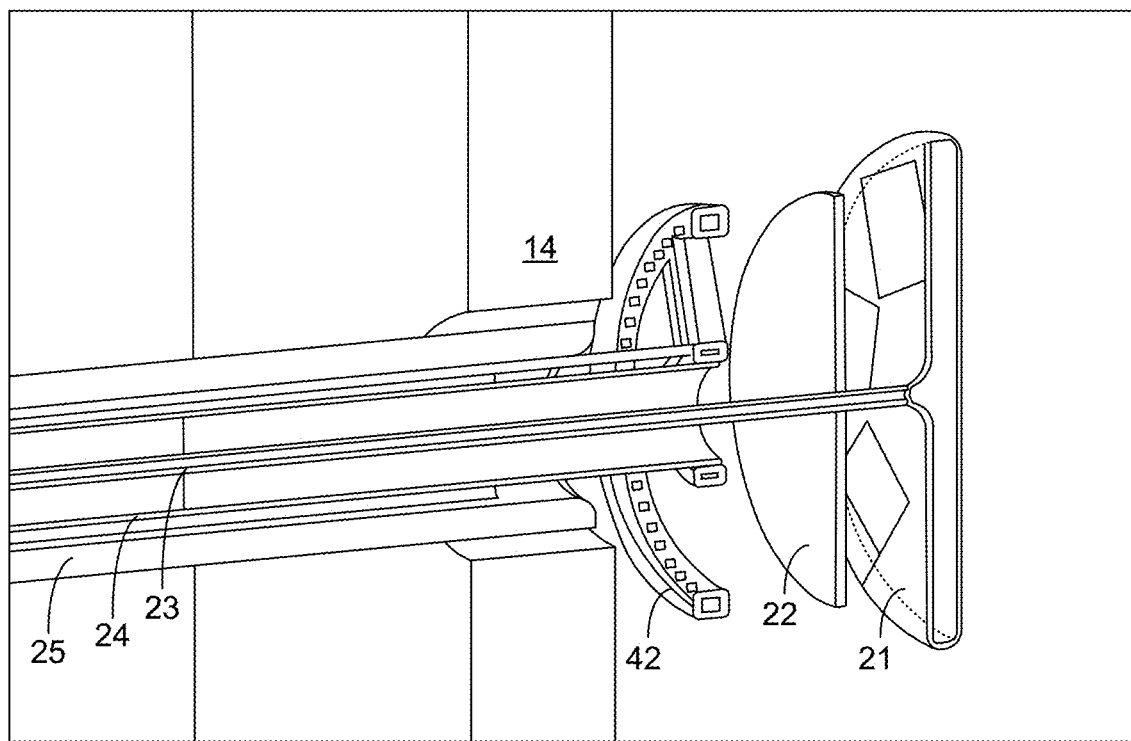
Figure 34:
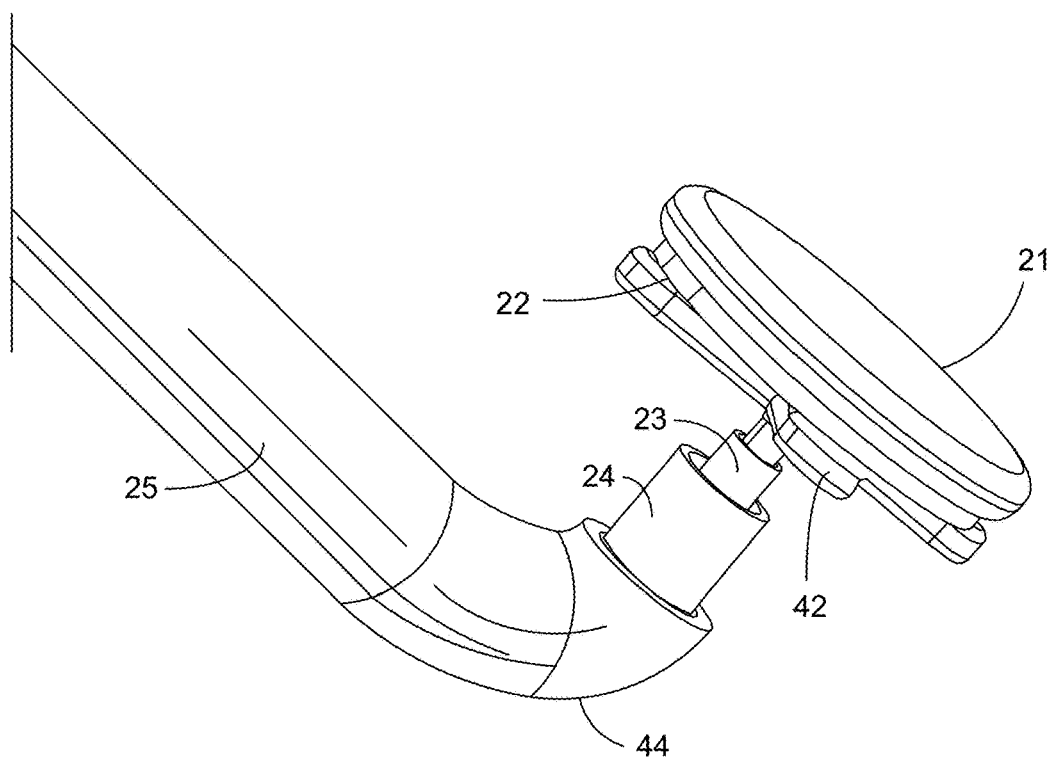
Figure 35:
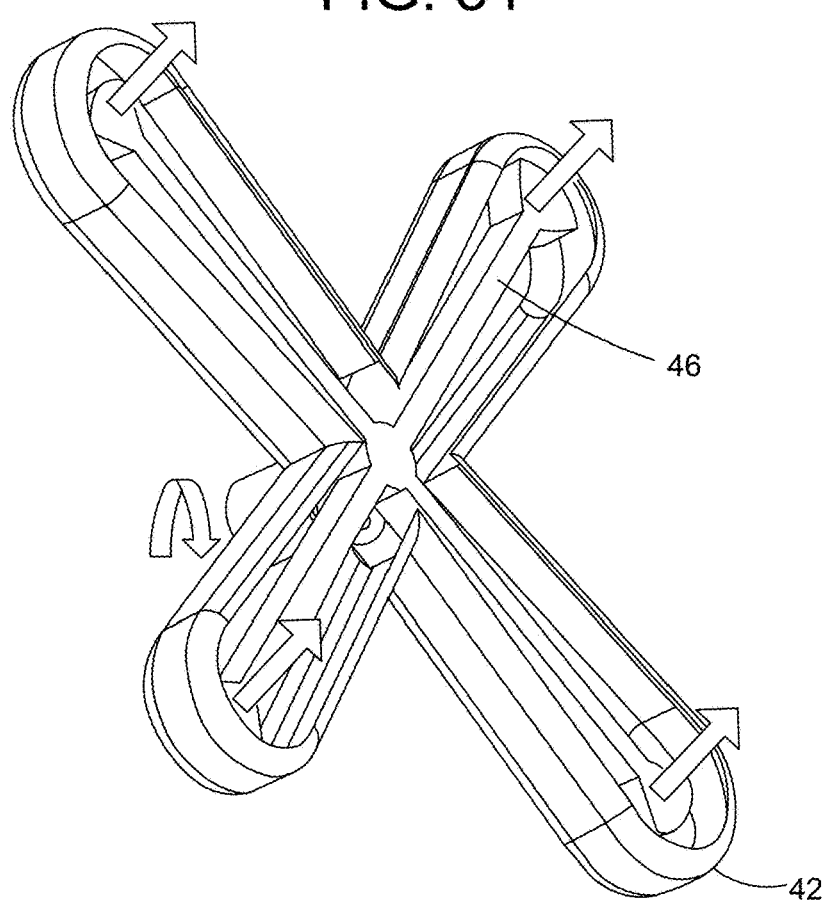
FIG. 35 is a sectional view showing the adhesive 46 flowing through the adhesive delivery dispenser 42 of FIG. 34.
Figure 36:
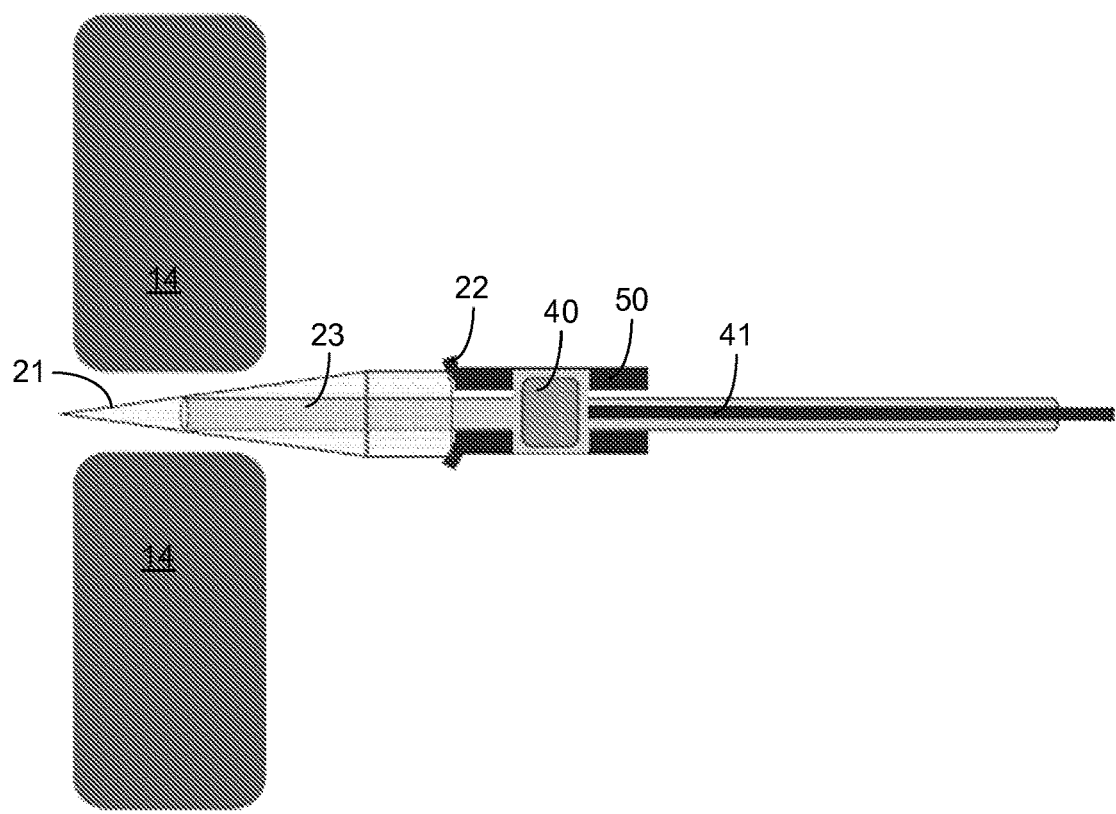
FIG. 36-39 illustrate use of an embodiment of the device to patch a septal defect.

A ring-shaped adhesive delivery dispenser 42 is shown in FIG. 31, wherein adhesive 46 is delivered through conduits 43 extending along the intermediate shaft 24 to the adhesive dispenser 42, which releases the adhesive 46 to flow into contact with the patch 22. Another embodiment of the adhesive dispenser 42 is shown in FIGS. 32 and 33, which also show tabs 48 on the distal balloon 21 with sutures 34 for patch attachment. Yet another embodiment of the adhesive dispenser 42 is shown in FIGS. 34 and 35, where the shafts 23, 24, and 25 include a steering angle (bend) 44 toward a distal end of the shafts adhesive 46 can be seen flowing through the dispenser 42 in FIG. 35.

The patch 22 can be designed to cover/bridge a defect 20 or to reinforce tissue; in additional embodiments, the patch 22 can be in the form of a flexible sensor (e.g., an electrical sensor for detecting electrical abnormalities on the surface of the heart) or a drug- or cell-delivery agent (where drugs or cells are coated on and/or contained by the patch 22) to monitor or treat the underlying tissue. The patch 22 can be formed of optically transparent poly-glycerol-sebacate urethane (PGSU), hydrogel or alternative optically transparent and flexible patch/sensor/drug or cell delivery device. Providing the patch 22 with transparency and elasticity enable proper activation and adhesion of the adhesive 46 to bind the patch 22 to, e.g., cardiac tissue. The patch's elasticity also enables leaving a minimal residual ventricular septal defect 20 after the distal balloon 21 is removed from the heart 12 passing through the patch 22 [e.g., through intersecting (e.g., cross-shaped) slits in the patch 22]. In some embodiments, two patches 22 can be employed, wherein one of the patches is applied on each side of the septum 14 or apical wall and pressed against the septum 14 or apical wall by respective balloons 21 and 40. In additional embodiments, the patch 22 can be in the form of a plug. In still more embodiments, the patch 22 can be in the form of a three-dimensional (3D) shaped patch with a self-sealing or valved feature in the patch 22 to seal after catheter retraction through the patch 22.

The light guide passing through the catheter to deliver light to the distal balloon 21 can be in the form of an optical fiber 29. The optical fiber 29 can have a conical sculptured fiber tip (or a tip that is otherwise optimized for light distribution in combination with the shape of the balloon/mirror) at its distal end (e.g., inside the balloon 21) that provides desirable light ray path to reflect the light onto the patch 22 on the septum 14 for curing. In other embodiments, the light guide is in the form of one or more bundles of optical fibers 29. In still more embodiments, the distal tips of the optical fibers 29 are flat or have another geometry, and the mirror is shaped to provide the desired light distribution.

Features to aid navigation can also be included, such as a guide wire lumen that enables tracking of the device along a pre-placed wire. The residual hole in the patch 22 can be sealed via a catheter that can apply and cure additional adhesive 46 following retraction through the patch 22 or through the use of a second patch 22, applied with a catheter on the opposite side of the tissue.

The device presented here has numerous potential applications, and although the experiments here were conducted with PGSU and HLAA, any optically transparent patch material (e.g., pericardium, dacron, polyurethane) can be used. The device is scalable, and the size or geometry of the distal balloon 21 or patch 22 can be specified based on patient-specific needs (e.g., from pre-procedural imaging).

Use of the Device:

In particular embodiments, the device is a multi-functional, catheter-based technology with no implantable rigid components that functions by (i) unfolding an adhesive-loaded elastic patch 22, (ii) deploying a double-balloon 21 and 40 to stabilize and apply pressure to the patch 22 against the tissue defect site and (iii) uniformly dispersing ultraviolet light via a fiber optic 29 and a reflective metallic coating for adhesion activation.

Figure 14:
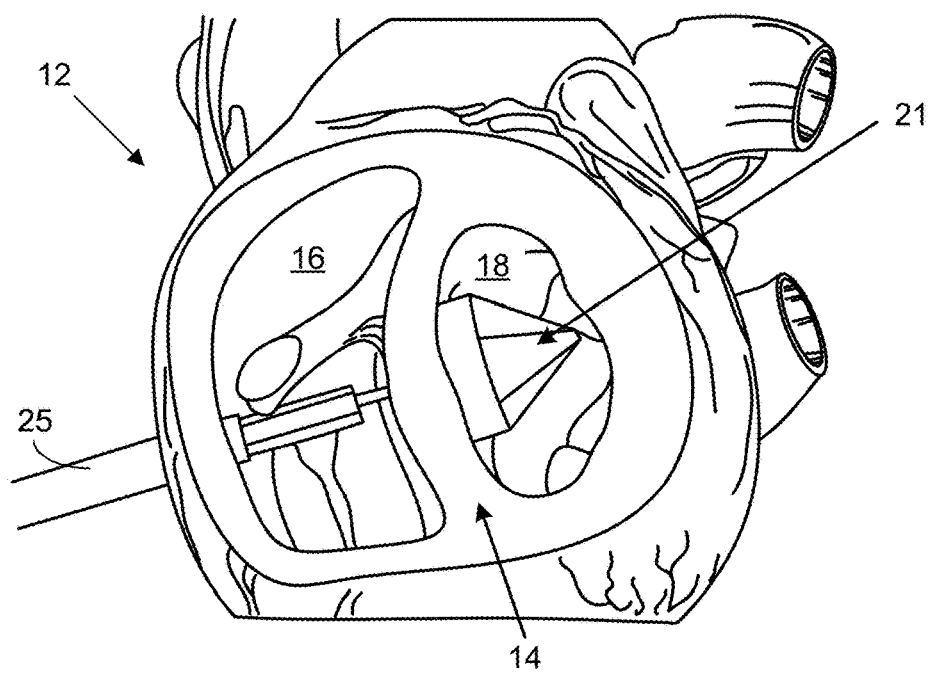
FIG. 14 is an illustration of the light-dispensing catheter device inserted through the right ventricle 16 and through a ventricular septal defect into the left ventricle 18 of the heart 12 to apply a patch to the septum 14.
Figure 15:
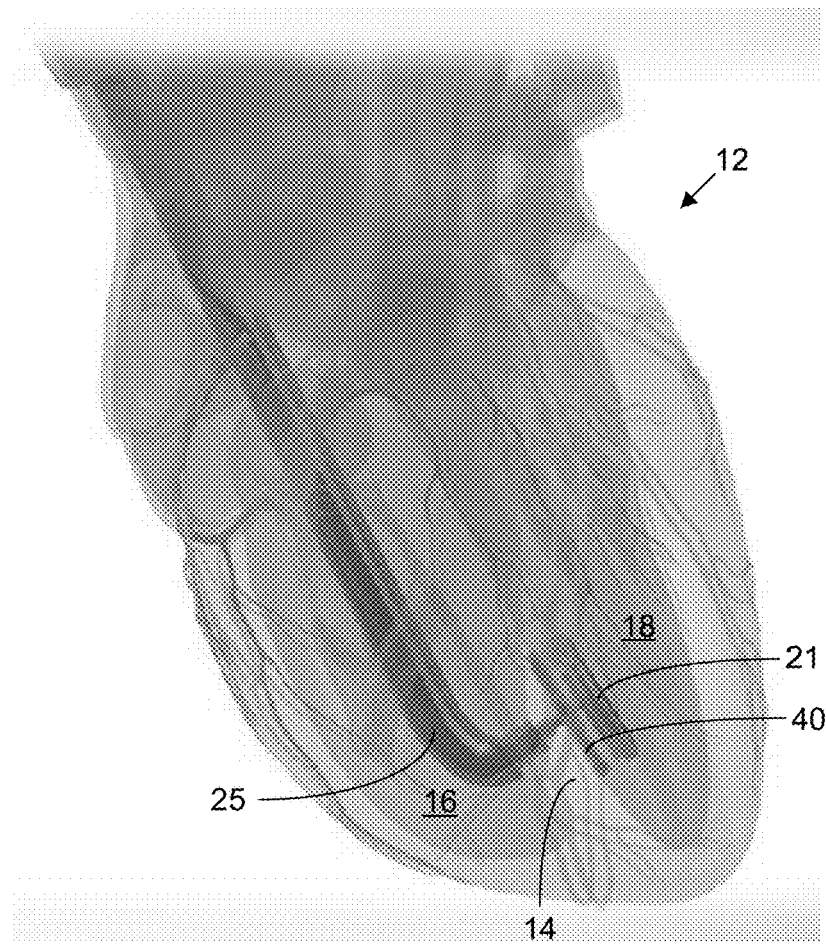
FIG. 15 is an image of the light-dispensing catheter device inserted via a right atrial/transvascular approach through the ventricular septal defect into the left ventricle 18 of the heart 12 to apply a patch to the septum 14.

As shown in the heart model 14 illustrated in FIG. 14, a perventricular surgical approach can be performed through a right thoracotomy; and the heart 12 can be exposed by opening of the pericardium. The procedure can be monitored and the delivery device visualized with. e.g., 2D- and 3D-echocardiography, 2D- and 3D magnetic resonance imaging, or with x-ray (fluoroscopy). Following the access route for the device into the heart 12 (via a synthetic cardiac model) shown in FIG. 14, the device enters the heart 12 via a trans-ventricular approach, where the distal balloon 21 and patch 22 are inserted through the right ventricle 16, through the ventricular septal defect 20, and into the left ventricle 18. In other embodiments, as show in FIG. 15, the device enters the heart 12 through a transvascular or transatrial approach. FIGS. 16-20 respectively show the following stages in a trans-ventricular approach: preparation, access, deployment, adhesion, and removal.

Figures 16, 17:
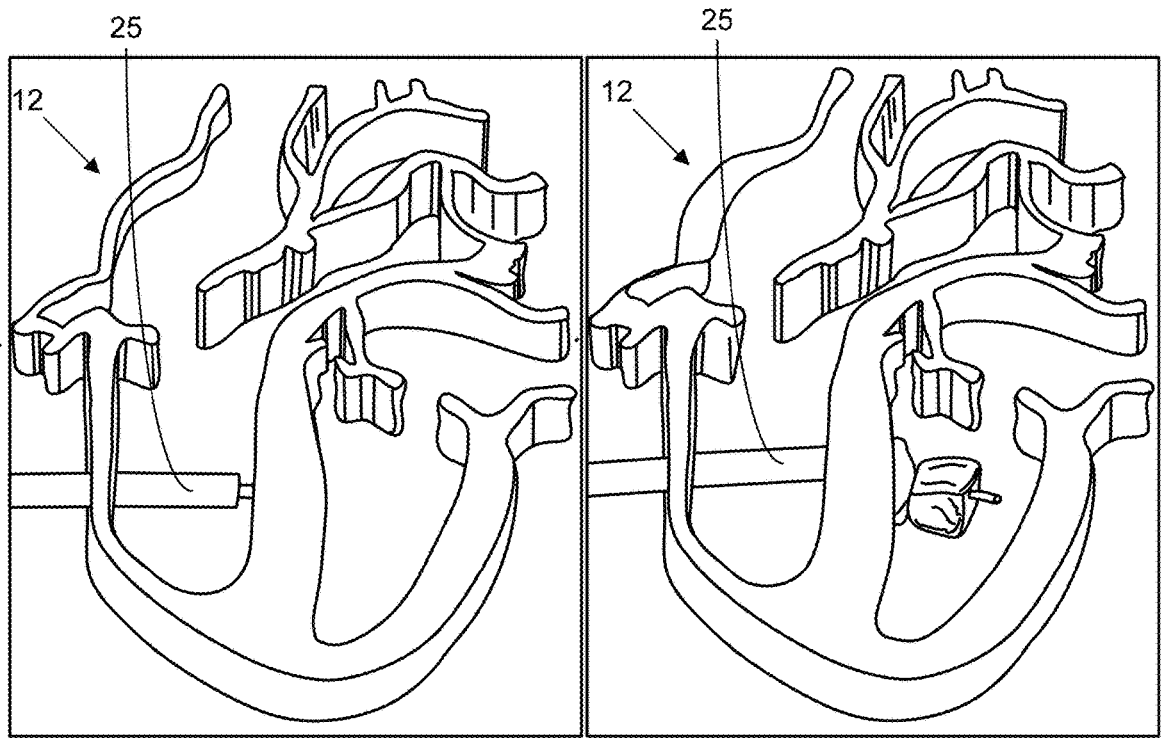
FIGS. 16-20 illustrate a sequence of steps in the repair patching of a ventricular septal defect.

As shown in FIG. 16, the device can then be introduced into the heart 12 from an incision in the right ventricular wall. The outer shaft 25 can remain inside the right ventricle 16, while the intermediate shaft 24 can be advanced over the guidewire through the ventricular septal defect 20 into the left ventricle 18.

As shown in FIG. 17, the inner shaft 23 can then be advanced, allowing the self-expansion of the patch 22, wherein the patch 22 is already covered with the adhesive 46 on the septal facing surface (folded into the intermediate shaft 24); and the distal balloon 21 is deployed.

Figures 18, 19:
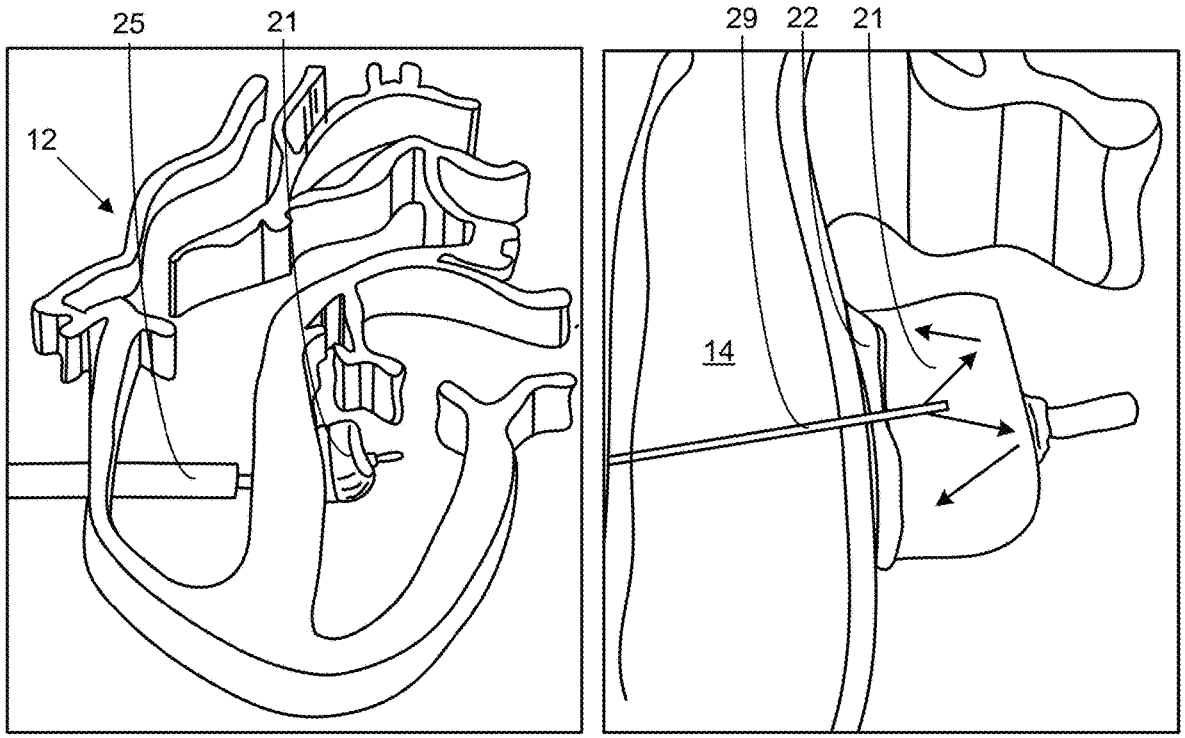
Figure 20:
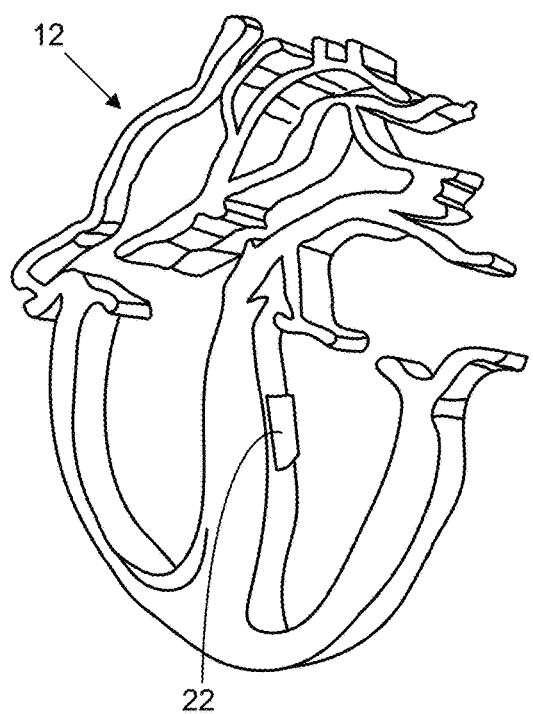
Figure 21:
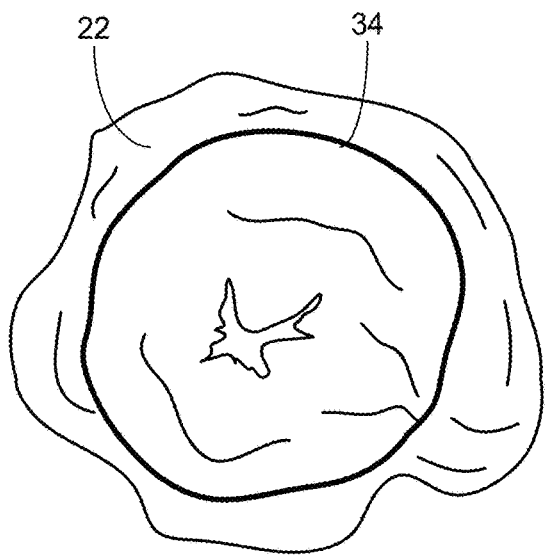
FIG. 21 is an image of a patch 22 for use with the device.

The distal balloon 21 can then be inflated and a UV fiber optic 29 (or other form of light guide) can be advanced into it. As the distal balloon 21 is inflated (e.g., by pumping a fluid, such as saline, into it), the distal balloon 21 can press against the patch 22 and tissue surface, as shown in FIG. 18. A second stabilizing balloon 40 can be simultaneously inflated on an opposite side of the septum 14. While compressing the patch 22 with the distal balloon 21, the UV light transmitted through the optical fiber 29 can be reflected by the aluminum surface coating on the distal balloon 21 onto the glue 46 (e.g., for up to 5 seconds) to cure the glue 46 while simultaneously applying pressure to the glue 46, as shown in FIG. 19. Finally, the suture 34 joining the patch 22 to the outer balloon layer 36 can be removed (by pulling one end of the suture 34 to release the patch 22 from the outer balloon 36); and the balloons 36 and 38 can then be retracted through the patch 22, leaving only a minimal residual defect 20, and the catheter can be withdrawn, as shown in FIG. 20.

Figure 12:
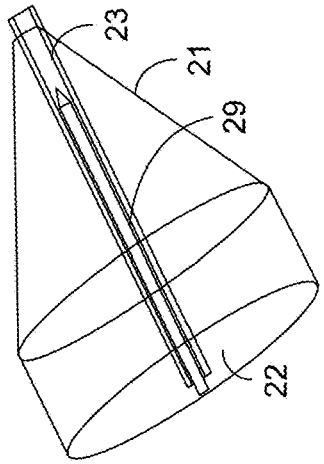
FIG. 12 is an illustration of an inflated balloon 21 with an optical fiber 29 inserted 118.5 mm into the balloon 21.
Figure 13:
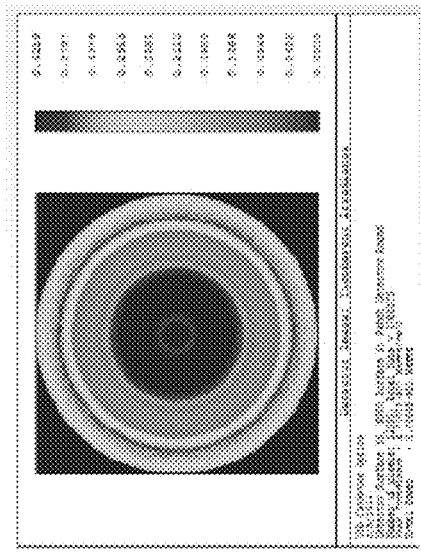
FIG. 13 is a plot of the light reflection pattern from the balloon 21 onto the patch 22 with the configuration of FIG. 12.
Figure 10:
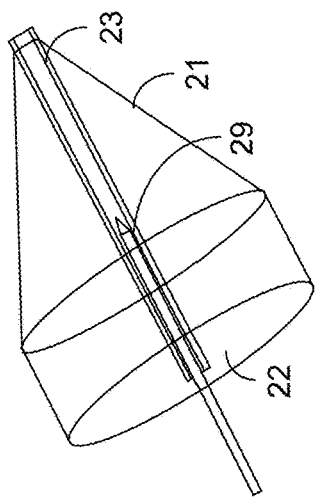
FIG. 10 is an illustration of an inflated balloon 21 with an optical fiber 29 inserted 10 mm into the balloon 21.
Figure 11:
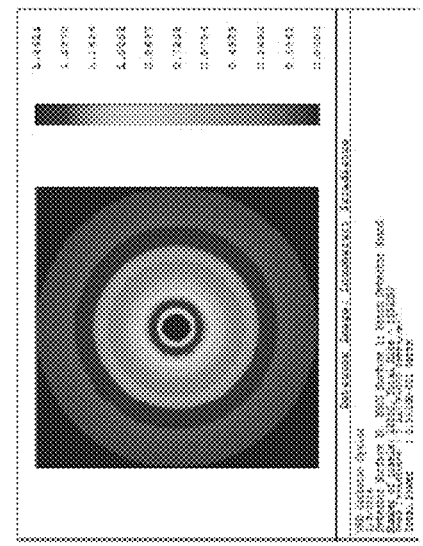
FIG. 11 is a plot of the light reflection pattern from the balloon 21 onto the patch 22 with the configuration of FIG. 10.
Figure 8:
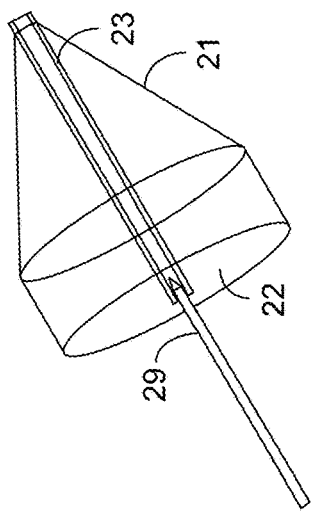
FIG. 8 is an illustration of an inflated balloon 21 with an optical fiber 29 at the edge of insertion (at 0 mm) into the balloon 21.
Figure 9:
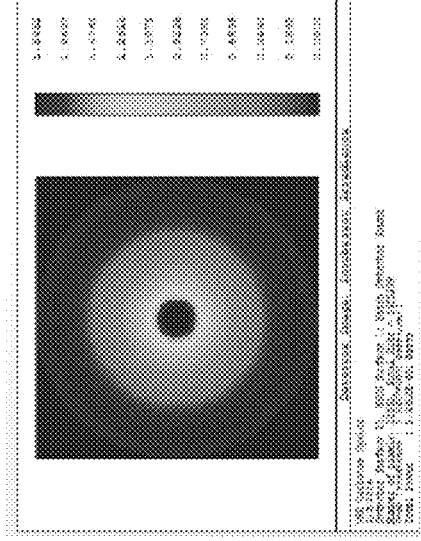
FIG. 9 is a plot of the light reflection pattern from the balloon 21 onto the patch 22 with the configuration of FIG. 10.

Extension of the optical fiber 29 into the distal balloon 21 at 0 mm, 10 mm, and 18.5 mm depth is shown in FIGS. 8, 10, and 12, with the resulting light distribution on the patch 22 shown in FIGS. 9, 11, and 13.

Figure 46:
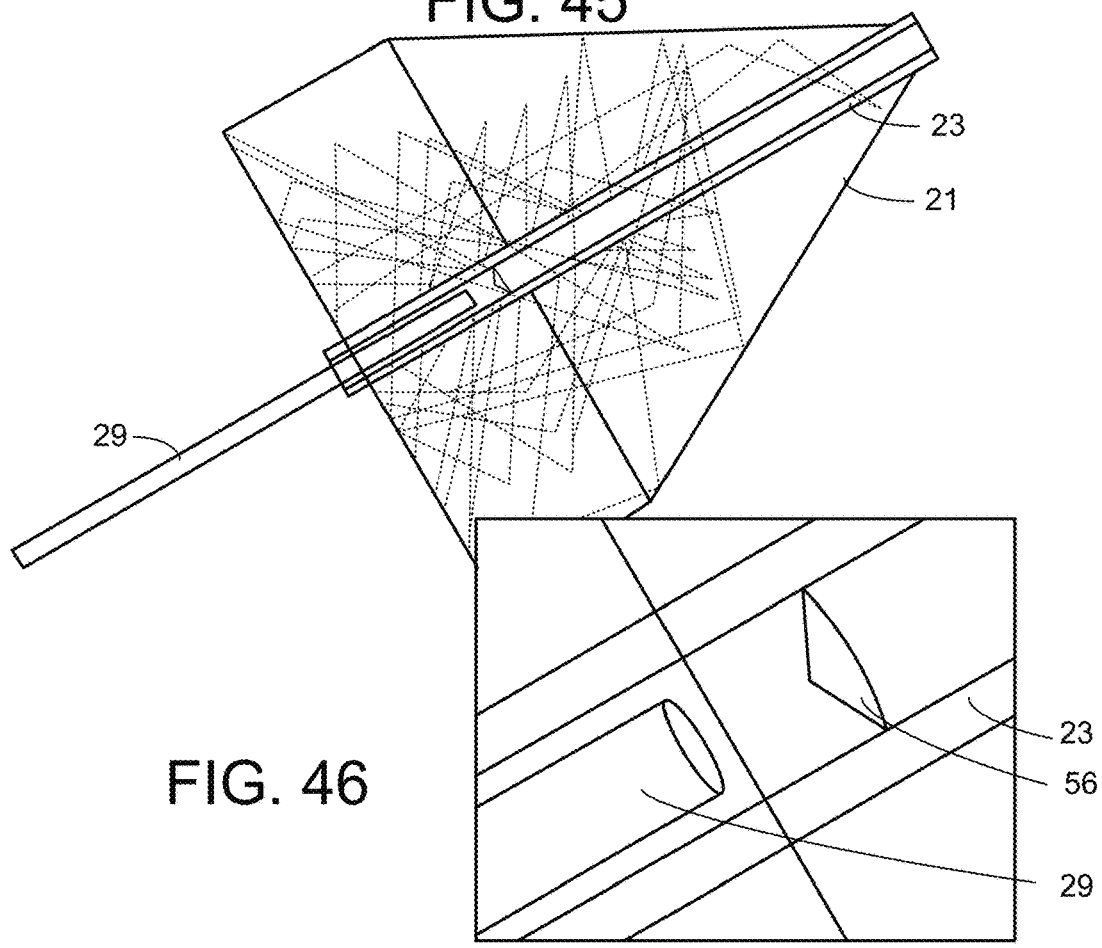
FIG. 46 illustrates an embodiment, wherein a partially reflective mirror 56 is mounted in the inner shaft 23 to reflect and diffract the light from the fiber optic 29 onto the inner reflective surface of the distal balloon 21.

An alternative design with a partially reflective mirror 56 in the inner shaft 23 is shown in FIG. 46, where the light is emitted from the end of the fiber optic 29 in an optically transparent inner shaft 23 to a partially reflective, conical mirror 56 that deflects and diffracts the light across a range of angles; and the light then bounces off the reflective surface of the balloon 21 to the patch 22 and adhesive 46.

Figure 26:
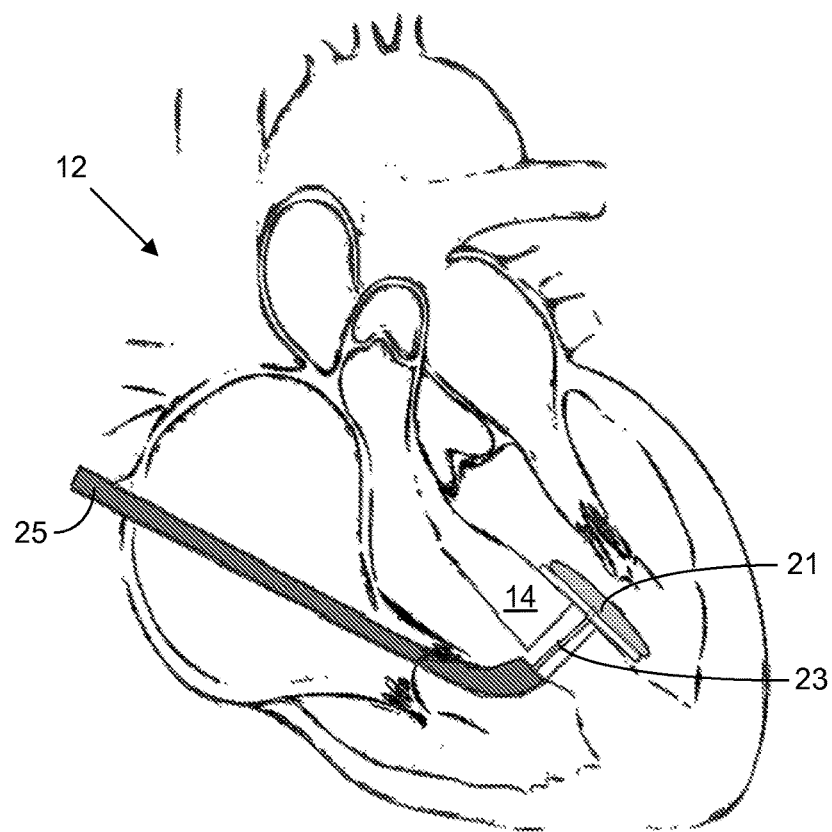
Figure 27:
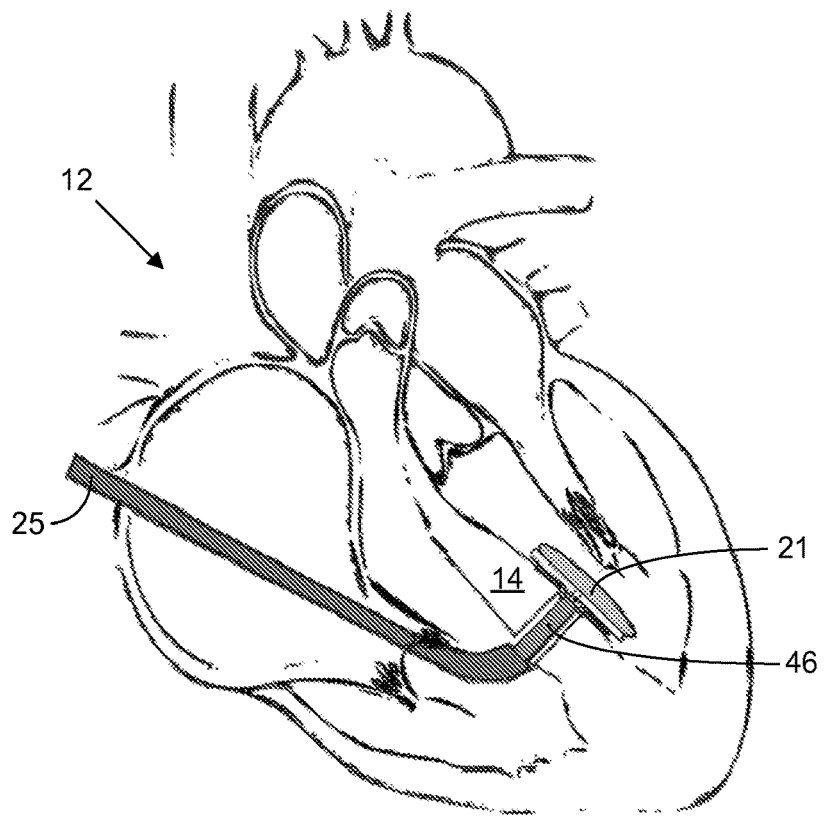
Figure 28:
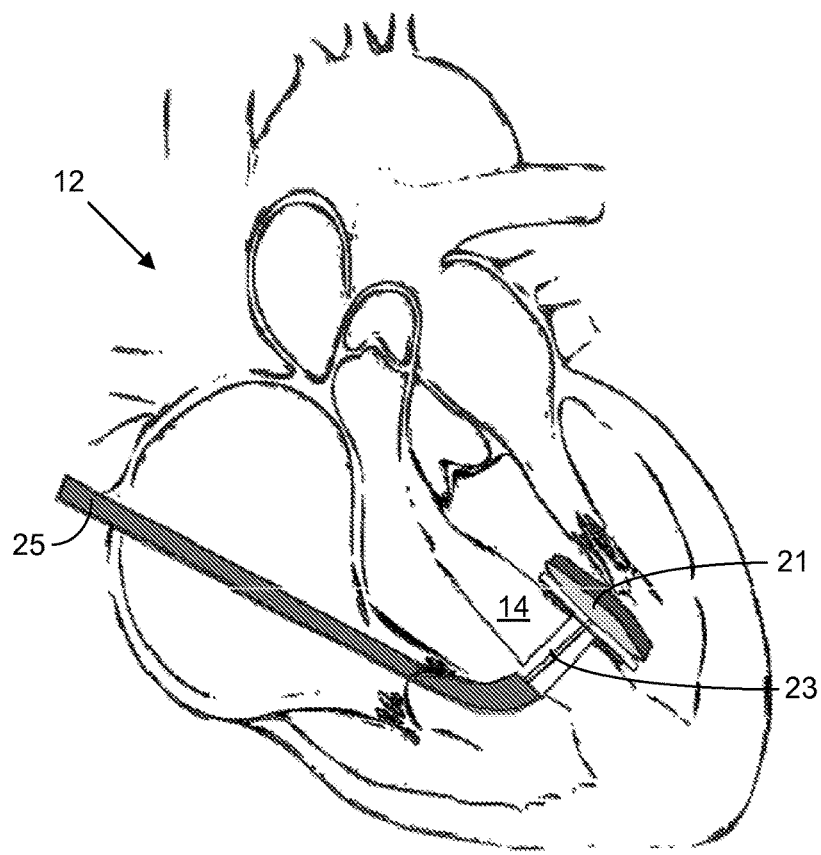
Figure 29:
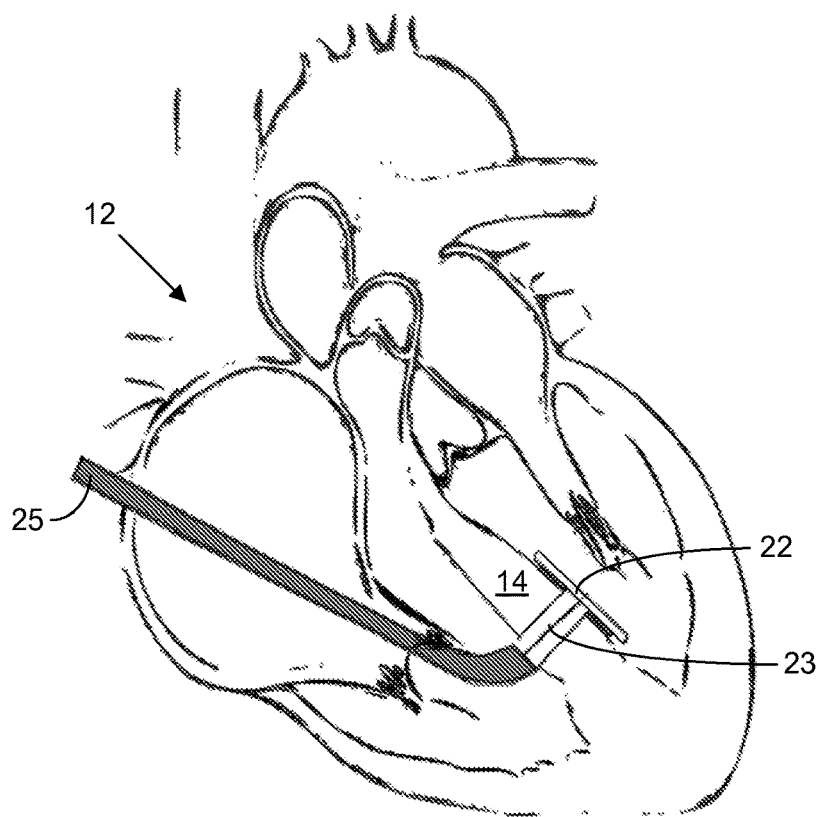
Figure 30:
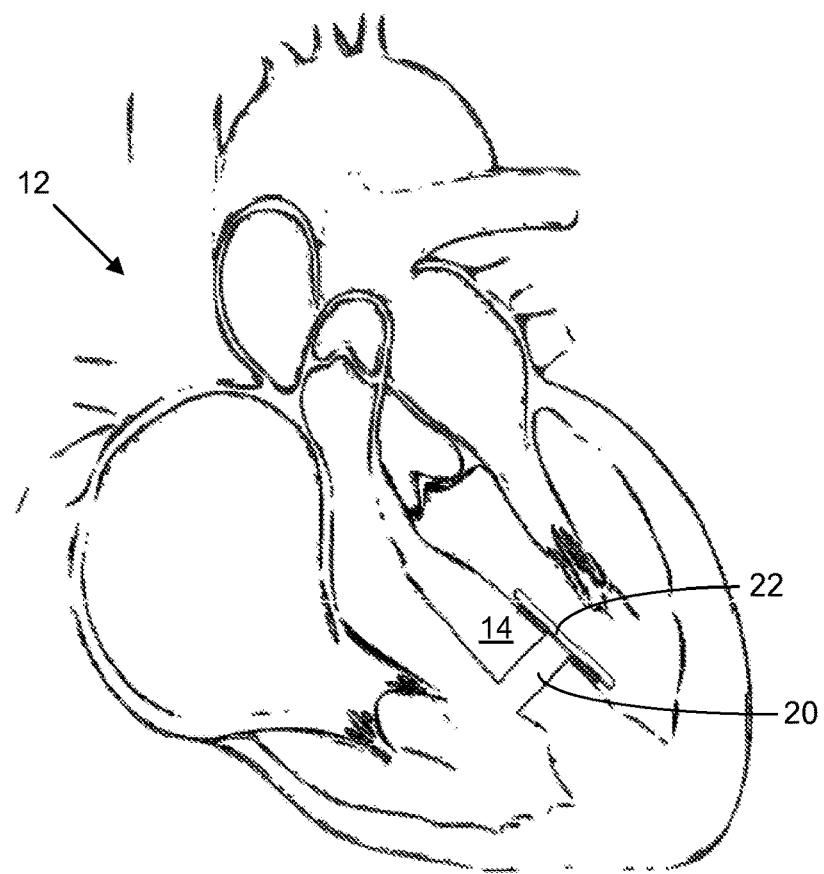

Stepwise schematics for an exemplification of a process for closing a ventricular septal defect 20 are provided in FIGS. 25-30. In an initial step, shown in FIG. 25, the device is inserted through the right atrial appendage and through the septal defect 20; next, the patch 22 is mechanically deployed to cover the septal defect 20. The anchoring balloon 40 is then inflated via a conduit passing through the patch 22, as shown in FIG. 26. Adhesive 46 is then flowed between the patch 22 and the septal wall surface contacted by the patch 22, while the inflated anchoring balloon 21 presses the patch 22 against the septum 14, as shown in FIG. 27. Next, an optical fiber 29, through which light (e.g., ultraviolet light) is delivered to the patch 22 and adhesive 46 to cure the adhesive 46 on the septal side, as shown in FIG. 28. The inner reflective coating of the distal balloon 21 prevents dispersion of light from the fiber 29 into the heart 12. The distal balloon 21 is then deflated and removed through a valve design in the center of the patch 22 to leave just the adhered patch 22 on the far side of the septum 14, as shown in FIG. 29. Finally, the device is removed, leaving just the adhered patch 22 in the heart 12, as shown in FIG. 30; and the atrial access point is sutured with purse string.

Figure 37:
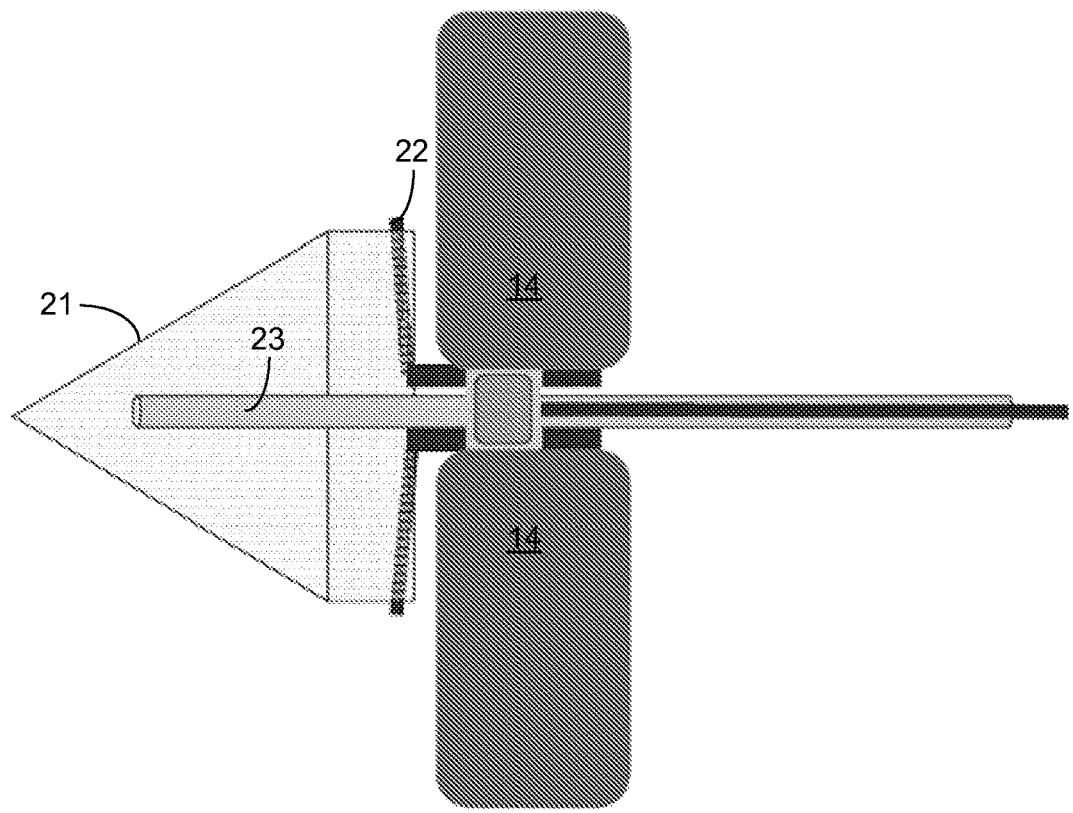
Figure 38:
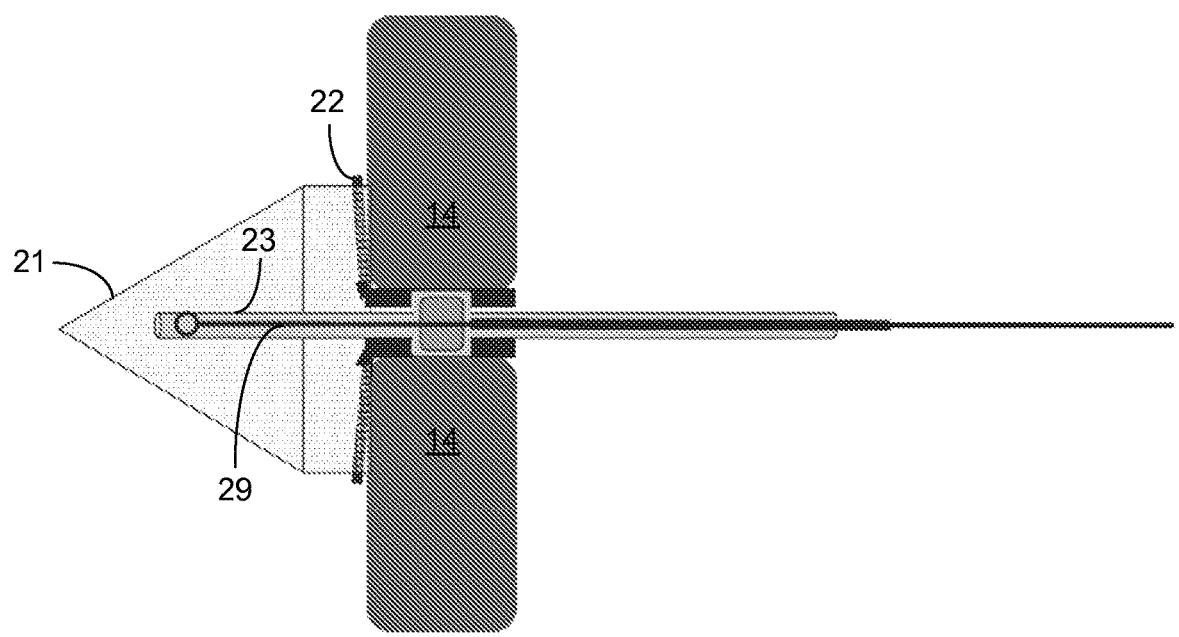
Figure 39:
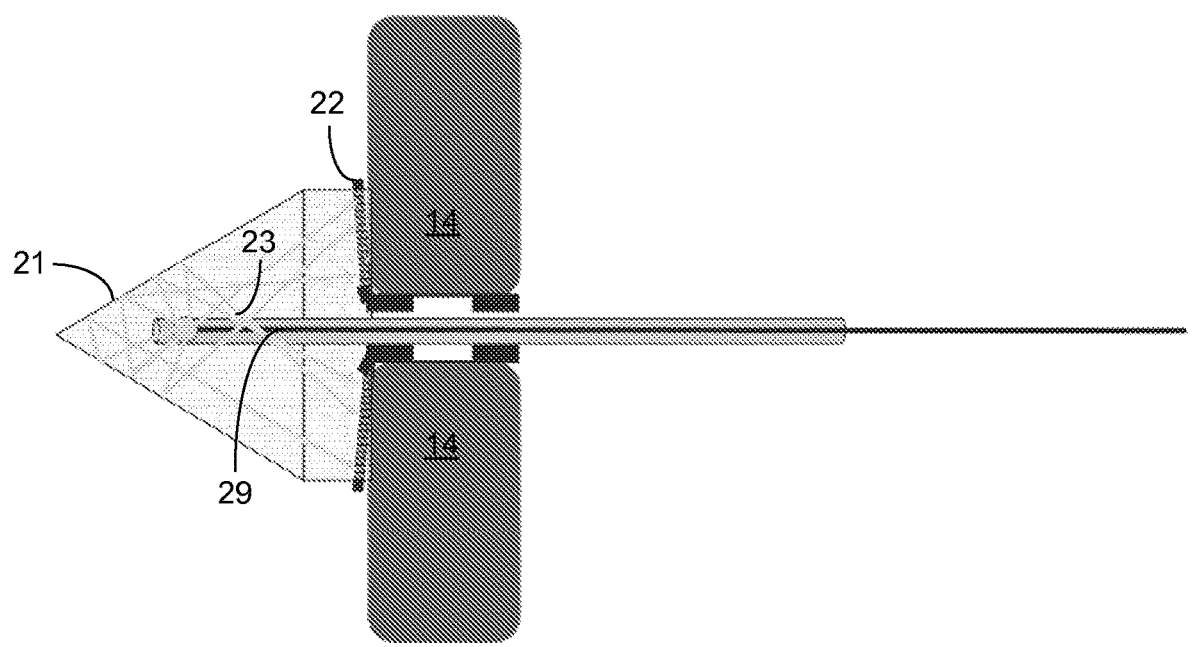

Additional illustrations of using an embodiment of the device to close a ventricular septal defect 20 are provided in FIGS. 36-39. In this embodiment, the patch 22 is in the form of a PGSU plug with collapsible wings that collapse and expand with the distal balloon 21 and with a neck 50 that extends along the shaft 23 to shield the shaft 23 from overflowing adhesive 46. In this embodiment, the proximal balloon 40 is mounted inside the neck 50 of the plug 22 and pushes outward on the neck 50 to secure the device in the septum defect 20. The proximal balloon 40 is also coupled with an inner pneumatic conduit 41 for delivering a fluid to inflate the proximal balloon 40. FIG. 37 shows inflation of the distal balloon 21 and the expansion of the plug wings 22, while FIG. 38 shows insertion of the fiber optic 29 through the shaft 23 into the distal balloon 21. Finally, in FIG. 39, light is transmitted through the fiber optic 29 and dispersed (reflected and refracted) at various angles around the distal balloon 21 until the light reflects off of the reflective inward-facing surface of the distal balloon 21.

Figure 40:
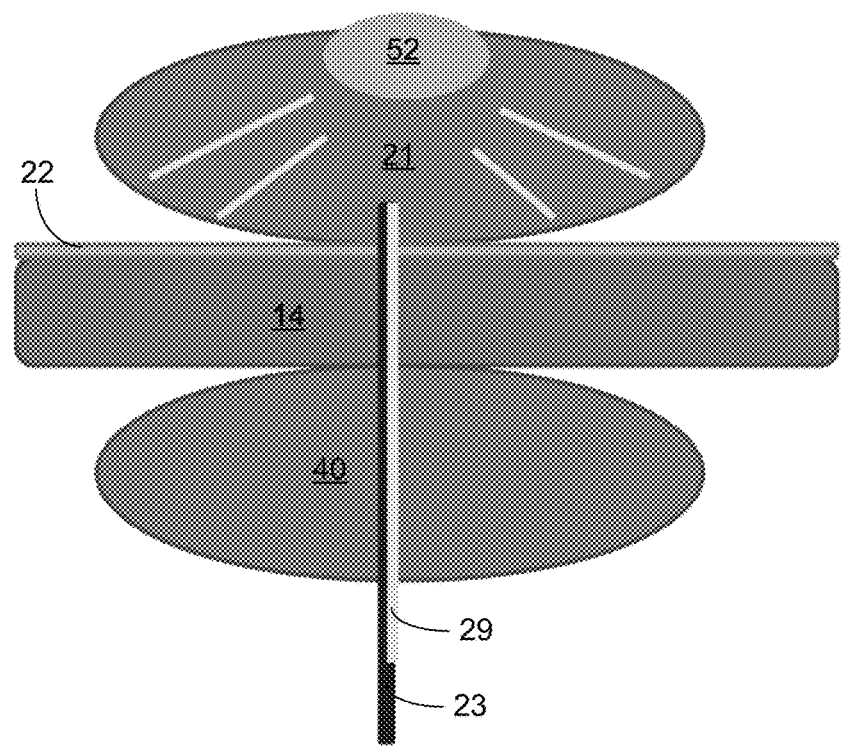
FIG. 40 illustrates an embodiment, wherein the distal balloon 21 includes a mirror 52 on the far side of the balloon 21 to reflect light from the fiber optic 29 back to the patch 22 and adhesive.

Another embodiment is shown in FIG. 40, wherein the distal balloon 21 includes a mirror 52 at the top of the balloon 21 (in the orientation shown). Light can be directed directly upward (in this orientation) from the optical fiber 29 across the balloon 21 into contact with the mirror 52, which disperses the light upon reflection.

Figure 41:
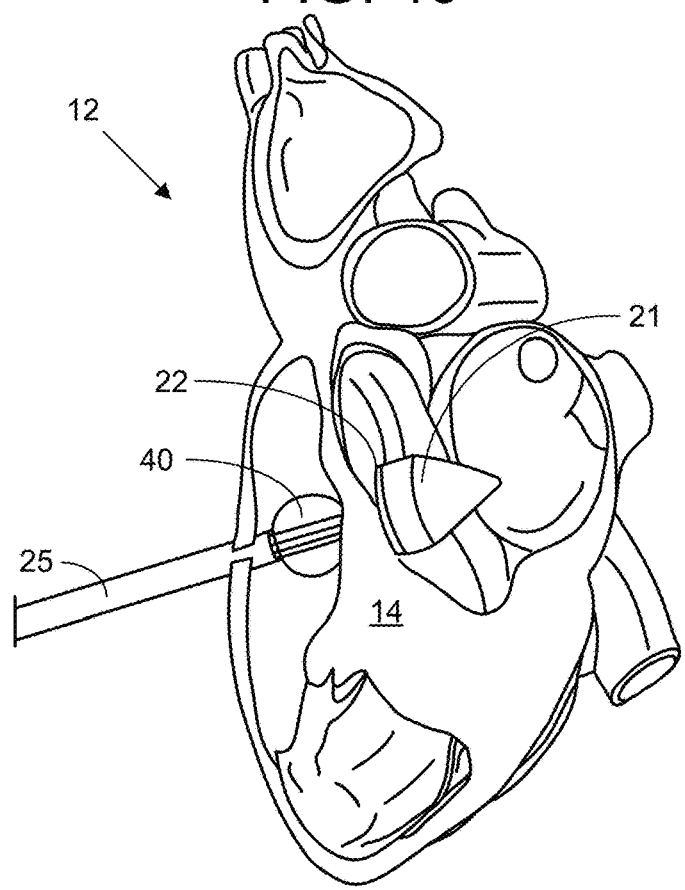
FIG. 41 illustrates an application where a light-transmitting/reflecting device to close an intracardiac defect in the septum 14.

Use of an embodiment of the device for intracardiac defect closure is further illustrated in FIG. 41, where the distal balloon 21 reflects light back on the patch 22 and adhesive 46, and where the patch 22 seals a hole in the septum 14 when the adhesive 46 cures. In another application, an embodiment of the device is used for epicardial patch delivery, as shown in FIG. 42. In this embodiment, the device need not pass through the wall to be patched. Rather, the distal balloon 21 and patch 22 remain on the same side of the wall as the shaft 25 so that the distal balloon 21, upon inflation, can press the patch 22 onto the outer surface of the epicardium. In this embodiment, the patch 22 can be applied for cell/drug delivery through the patch 22 to the epicardium or for ventricle reinforcement for heart-failure patients. In this embodiment, the light is focused forward inside the distal balloon 21 to the far side of the distal balloon 21 where the patch 22 is attached. Without a component of the device to provide stabilization on an opposite side of the epicardium from the patch 22, a suction tool incorporated into the device can provide a suction bond with the epicardium to stabilize the patch 22. The device can also incorporate a central needle or multiple microneedles for cell/drug injection.

Yet another example of an application for the device is shown in FIGS. 43 and 44. In this embodiment, the device is used for apical closure, e.g. after a transcatheter aortic-valve implantation procedure. An intraventricular patch 22 is applied with the device of FIG. 43; and the residual hole in the patch 22 is sealed with a patch 22 (without a center aperture) applied from the opposite side by the device of FIG. 44. The patches 22 applied by both devices can be linked with a suture 34 or with an extension of the patch material.

Figure 45:
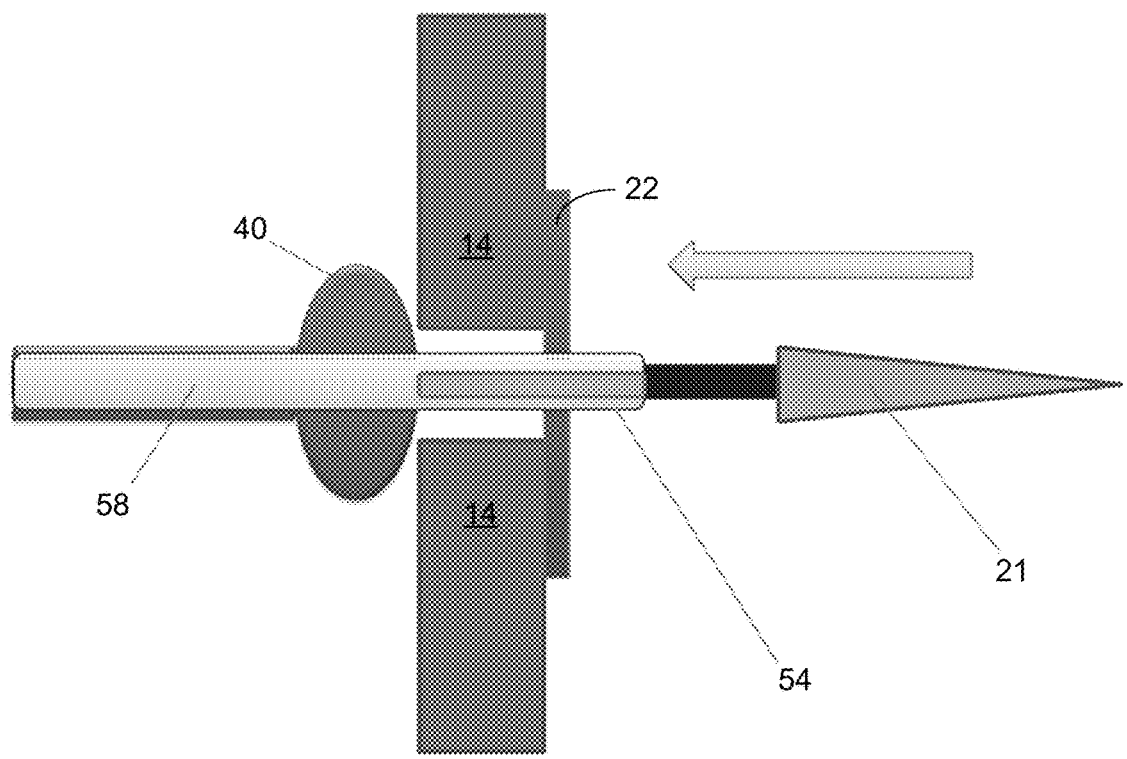
FIG. 45 illustrate an embodiment of the device, wherein a retrieval catheter 58 is used for retrieving the distal balloon 21 after the patch 22 is secured.

In FIG. 45, an intermediate retrieval catheter 58 is used to achieve a uniform profile of deflated distal balloon 21 during retrieval. In this embodiment, the distal balloon 21 is pulled into the retrieval catheter 58; and the retrieval catheter is pulled back through the patch 22 while the proximal balloon 40 provides stabilization. The intermediate retrieval catheter 58 includes an expansile distal tip 54 with lower durometer or co-extruded material to accommodate entry of the distal balloon 21 there into.

Preliminary Studies:

To quantify adhesion strength, we used polyglycerolse-bacate urethane (PGSU) as a surface-eroding, biodegradable, biocompatible and UV-transparent patch material and coated the patch 22 with poly-glycerol-sebacate acrylate. The patch 22 was attached to porcine cardiac tissue. Adhesion strength was determined by standard pull-off tests.

Figure 22:
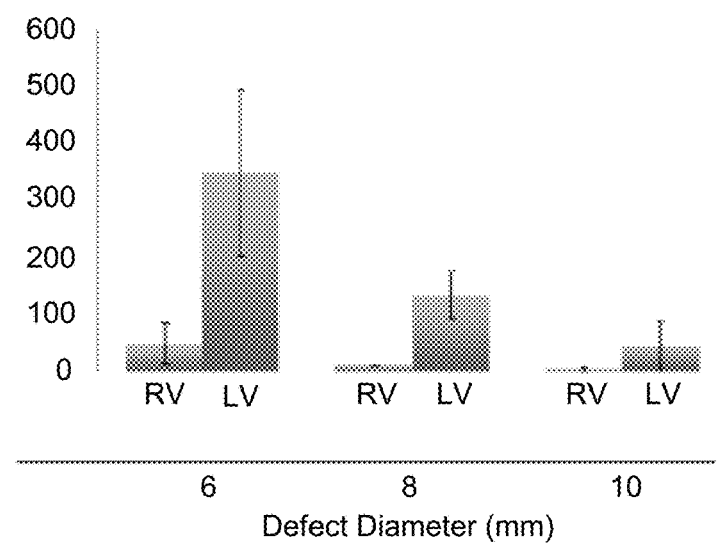
FIG. 22 is a plot of the burst pressure that a 14-mm-diameter patch on a ventricular septal defect could withstand in the right ventricle (RV) and in the left ventricle (LV) for defect diameters of 6, 8, and 10 mm.

A test was set up for patch-to-VSD size optimization, wherein a ventricular septal defect 20 was created on porcine cardiac tissue and mounted on a closed system and pressurized until patch dislodgment. The diameter of the patch 22 was 14 mm. The results are shown in FIG. 22, where the right ventricle (RV) burst pressure is shown via the left-side bar for each defect size, and where the left ventricle (LV) burst pressure is shown via the larger right-side bar in each pair. As anticipated, due to the pressure advantage in the left ventricle (LV) 18, in vitro burst experiments show a significant advantage of patch attachment to left (LV) versus the right (RV) side of the septum 14. A left-sided patch can withstand burst pressure of over 300 mmHg. The ideal patch/VSD size ratio was found to be about 2.2, as indicated by the bar graph.

A polyglycerolsebacate urethane patch 22 was attached to the intact ventricular septum 14 of a pig during beating heart surgery and confirmed by intraoperative trans-epicardial 3-D echocardiography.

Figure 23:
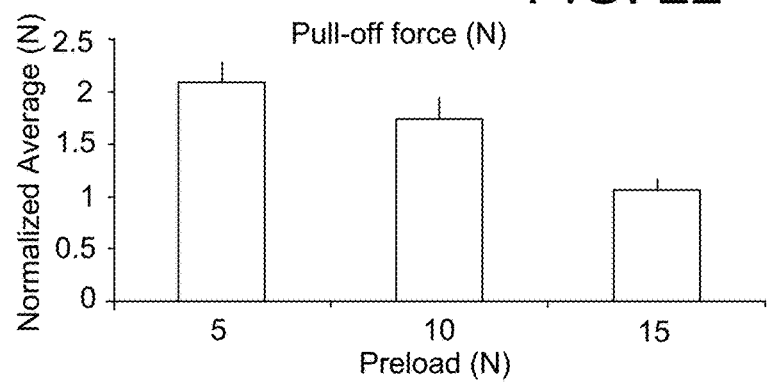
FIG. 23 is a plot of the pull-off force required to pull of an applied patch after light curing of the adhesive 46 with preload forces of 5, 10 and 15 N.

Results from a pull-off test in which a patch 22 was applied to a septum 14 under various preload forces are plotted in FIG. 23.

Figure 24:
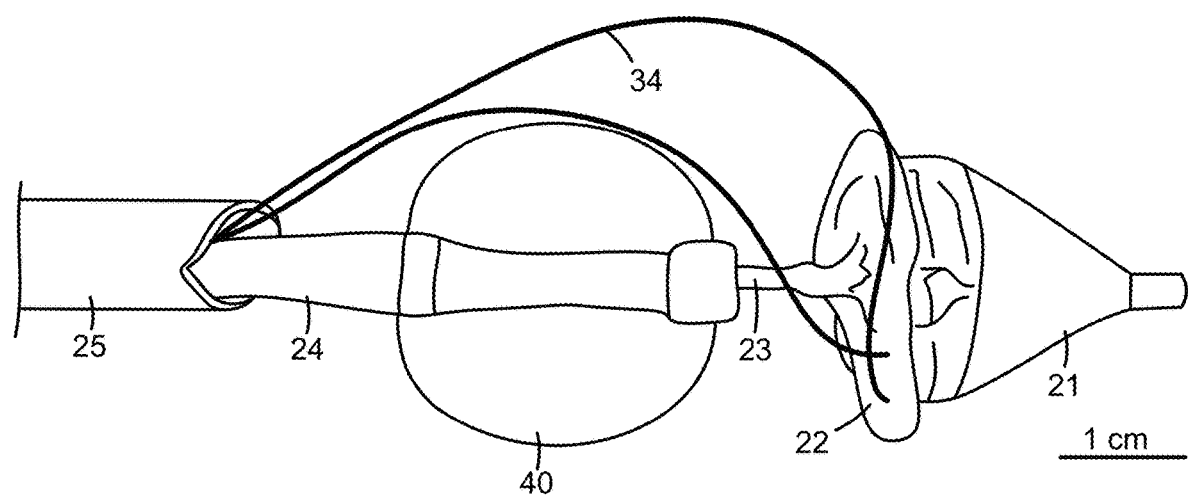
FIG. 24 is an image showing components of an embodiment of the device, including a proximal balloon 40, an intermediate shaft 24, a distal balloon 21 including a secondary outer balloon, removable sutures 34 for temporary path/balloon coupling and a patch 22 with a photocurable adhesive.
Figure 25:
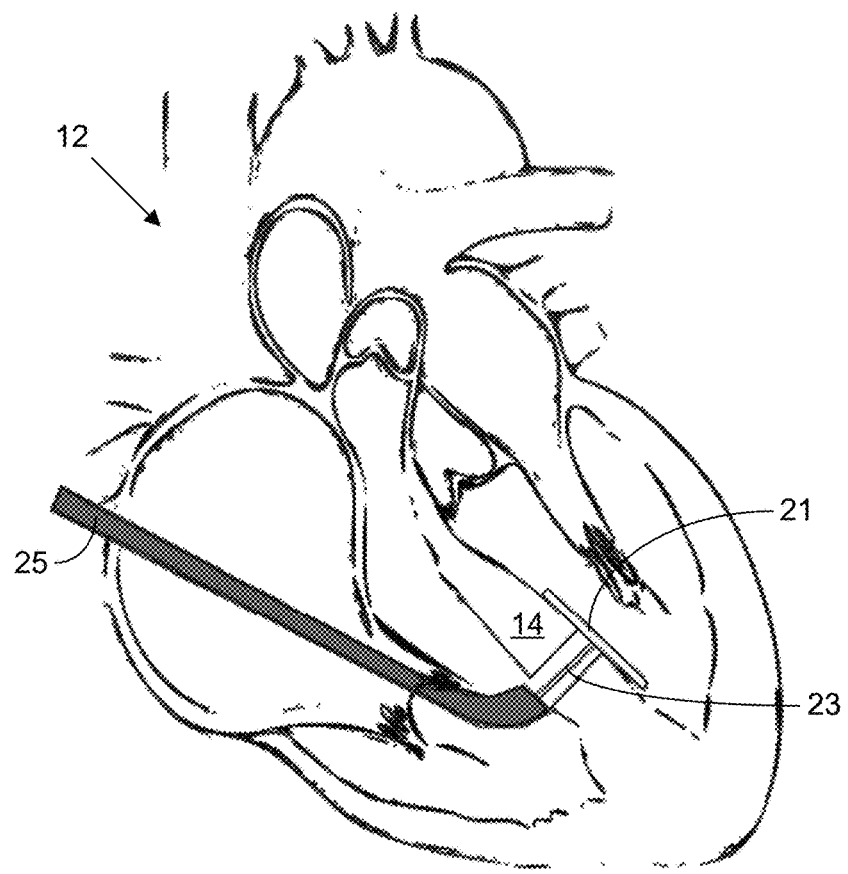
FIGS. 25-30 provide a schematic step-wise series of sectional illustrations of a ventricular septal defect closure.

Exemplification Results:

In a catheter-based device, ultraviolet light can be delivered via an internal fiber optic 29 to a reflective balloon 21 where it is reflected onto a patch 22 pre-coated with photocurable adhesive 46 to affix the patch 22 to the tissue, prior to removal of the device. The functional components of the device include a reflective distal balloon 21 fixed on an inner shaft 23 and a proximal stabilizing balloon 40 on an intermediate shaft 24 (FIG. 24). All components can be loaded into an outer shaft 25. A UV fiber optic 29 (connected to a UV source 30 at one end and designed for light dispersion at the other) is housed in the inner shaft 23, and can be advanced into the inner lumen until the tip is located in the distal balloon 21. The reflective distal balloon 21 has an outer layer that allows temporary suture-based attachment of a patch/adhesive system (FIG. 24), ensuring the patch 22 unfolds with the distal balloon 21 and can be released from the system in situ.

All components can be deflated and loaded into the outer catheter shaft 25 for delivery. The procedural steps are as follows: (i) the catheter is delivered through the defect 20; (ii) the patch 22 is released by pulling back the open suture loop connecting the patch 22 to an outer membrane on the reflective balloon 21; (iii) balloons are deployed (distal balloon 21 first, then proximal balloon 40); (iv) UV light is turned on to activate the photocurable adhesive 46 coated on the proximal side of the patch 22; and (v) both balloons 21 and 40 are fully deflated and removed from the body. In the last step, the distal reflective balloon 21 is retrieved through a four-leaflet valve in the patch 22, leaving the patch 22 adhered to the tissue. Each shaft 23, 24, and 25 was connected to an ergonomic handle 26, which allowed coupling and uncoupling of each shaft, and enabled volume-controlled inflation and deflation of the balloons 21 and 40 via a syringe 32.

Development and Optimization of a Light-reflective Flexible Medical Balloon:

Plasma pre-treatment of the urethane balloon substrate, which enhances adherence of a metallic coating to the urethane substrate, was performed to improve the reflectivity of both aluminum and palladium. To select an outer protective coating to prevent aluminum/blood contact urethane, gold and poly(p-xylylene) were coated on aluminum samples and the reflectivity test was repeated. All outer coatings resulted in similar reflectivity.

Aluminum particles were deposited on the balloons when a direct current was applied under vacuum (4 mtorr). Urethane balloons were masked on their flat face and taped onto a rotating mount in a sputter chamber. In the final multi-step coating process, a urethane balloon was pre-treated with plasma, coated with 100 nm of aluminum, and a second outer urethane balloon was applied to act as a barrier between the coating and the external environment and to participate in the patch deployment/release mechanism. The coating thickness varied slightly, but predictably, with distance from the aluminum source, and the adhesion of the coating was improved with poly(p-xylylene) pre-treatment.

Optimization of a Low Profile Fiber Optic Cable for Light Dispersion:

To disperse the reflected light on to a relatively large area, the internal fiber optic cable 29 delivering the light was sculpted. By shaping the tip of the internal fiber optic 29 and moving it relative to the reflective chamber (varying the insertion distance), reflected light rays are spread over a larger area compared to a flat tip. Light ray trace simulations were used to examine the effect of the fiber tip angle (straight and 20° conical tip) and the fiber depth (0, 10, and 18.5 mm, as measured from the flat face of the distal balloon 21) for a given inflated balloon geometry. The efficiency calculations assumed that 100% of the light is available in the fiber 29 before the light is launched into the catheter. The resulting light irradiance maps demonstrated that a sculpted conical fiber results in more spreading of the light on the adhesive/patch system compared to a flat fiber tip. The favorable spreading of light and light reflectance at each fiber insertion depth was compared. The flat tip had more variability in efficiency, as it is sensitive to fiber position within the inner shaft 23. The conical tip had greater efficiency, and less sensitivity to position in the inner shaft 23.

The final design of the fiber optic 29 was a sculpted conical shape, which enabled spreading of light over the entire surface of the 25 mm-diameter circular patch 22 by simply moving the fiber 29 along the inner shaft 23 inside the reflective distal balloon 21. The motion of the fiber 29 acts to 'paint' a uniform irradiance on the patch 22. Relative to the purely conical balloon shape, the slightly curved shape of the inflated balloon 21 has a small effect on the efficiencies or ray patterns. Depending on balloon geometry and clinical application, the fiber optic tip can be sculpted in a case-specific manner using such simulations.

Device Assembly:

For the experiments in this study, HLAA and a UV light transparent patch 22 made of PGSU were manufactured. Additionally, PGSU patches 22 were laser cut to diameters specified. Eight 0.5-mm holes around the perimeter of the patch 22 and a four-leaflet valve with <5 mm slits were laser cut in the center to allow device insertion and withdrawal with minimal residual shunt.

The inner shaft 23 (Clear pebax 72D shaft; inner diameter 1.42 mm, outer diameter 1.67 mm, length 34 cm, from Vention Medical) was bonded to an aluminum-coated urethane balloon 21 (#20000701AD from Vention Medical with both necks trimmed to 2 mm) using light curable adhesive 46 (Loctite 3943 from Henkel AG & Co. KGaA) at each neck 50, after skiving the distal end to allow balloon inflation. An identical outer balloon 36 was sutured to the laser cut patch 22 with eight continuous sutures 34 (Prolene 5.0, RB2 from Ethicon US, LLC) around the perimeter of the patch 22, guided by laser cut holes in the patch 22, as shown in FIG. 24 with temporary sutures 34 threaded through the holes. The patch/outer balloon assembly was placed over the coated balloon 21 on the inner shaft 23 and bonded at the distal end with the Loctite 3943 adhesive 46.

Representative Clinical Applications Ex Vivo:

Adhesion to explanted sections of pig heart, abdominal wall and stomach was tested by activating a hydrophobic light-activated adhesive 46 (HLAA) attached to a poly(glycerol sebacate urethane) (PGSU) patch on the surface of the tissue sample with the catheter balloon device. To quantify the adhesion force, pull-off testing was conducted on tissue samples after a 3N pre-load application, with forces ranging from 0.59-2.54N. Patch attachment was successfully achieved for all samples (n=3 per tissue type). Successful patch attachment for the heart and abdominal wall was measured by manual pull-off assessment. For the stomach, the balloon 21 was filled to a supraphysiological volume (>1 litre) and demonstrated to be watertight.

A patch was attached to a whole excised porcine heart (n=3 hearts) and to the septum of a heart pressurized to physiologically relevant levels (20 mmHg and 120 mmHg in the right and left ventricles, respectively) under echo guidance. An abdominal wall reinforcement procedure was performed in a euthanized porcine model carcass to evaluate the spatial interaction between the device and abdominal organs. A small incision was made in the skin of the abdomen and a surgical tunnel was created through the abdominal wall layers for the device insertion. Feasibility of the procedure and patch attachment to the innermost layer of the abdominal wall was successfully demonstrated. The PGSU patch is designed to degrade over time but could be exchanged for a synthetic hernia mesh.

The balloon catheter was evaluated as a potential endoscopic tool for tissue closure during natural orifice translumenal endoscopic surgical (NOTES) treatment of lesions of the gastro-intestinal tract. The procedure was performed on an entire porcine stomach, both in a whole deceased animal or with the full stomach on the lab bench. In both cases, the device was inserted through the esophagus and directed toward a defect artificially created on the anterior free wall of the stomach. The patch was firmly attached on the external surface of the stomach. Additional adhesive was applied with a syringe to seal it, and cured directly with the fiber optic (ultimately this could be achieved with application of a second patch). The stomach was filled to capacity (>1 liter) to test patch adhesion to tissue under supraphysiological hyper-distension, and no leaks were observed.

Demonstrative Representative Clinical Applications Ex Vivo:

Isolated fresh porcine abdominal wall, stomach, and cardiac tissue (n=3) samples were collected from euthanized pigs. A PGSU patch (200 μm thick and 20 mm in diameter) was attached to the tissue by activating a thin layer of pre-coated HLAA with the device (120 seconds activation at 3N pre-load) connected to a UV-light source (OmniCure S2000 from Lumen Dynamics Group Inc.), with a filter in the range of 320 to 390 nm. The tissue samples were kept wet with saline before and after patch adhesion. Standard pulloff adhesion testing was performed on an Instron 5566. Briefly, the adherent PGSU patch was attached to a flat probe using cyanoacrylate glue (Loctite 4601) a compressive preload of −1N was applied for 5 seconds and the patch was pulled off at a rate of 8 mm/min. Maximum force was recorded.

For an ex vivo isolated heart model, fresh whole porcine hearts (n=3) were used. Procedural steps were performed (i) under direct vision with ventricular walls removed (n=2) or (ii) blindly (n=1). To simulate the pressurized heart, a fresh porcine heart was explanted; both the aortic valve leaflets were removed, and the pulmonary artery and aorta were securely connected to saline columns at 20 and 100 mmHg respectively. Echocardiography was used to image the procedure. The patches were fully adhered.

For an ex vivo abdominal wall reinforcement model, the procedure was performed in a porcine carcass to evaluate patch attachment to the innermost layer of the abdominal wall (parietal peritoneum). A midline incision of the abdominal wall was performed to visualize the procedure). A 6 mm incision was made on the skin of the abdomen and a subcutaneous tunnel was created to facilitate device insertion.

For an ex vivo endoscopic closure of a stomach defect, isolated fresh porcine stomach (n=2) was used for testing procedural feasibility and patch attachment to the outer surface (visceral peritoneum) of the stomach. In an animal carcass, an incision of 5 mm was made on the anterior free wall of the stomach. The device was inserted through the esophagus, and patch was attached to the outer wall. To represent a distended stomach, the organ was explanted and mounted on a hanging support, and the pylorus was attached, and sealed, to a syringe. The patch was adhered with a catheter. 1 ml of HLAA was added to the valve in the patch from the outside with a syringe and cured directly with the fiber optic from the device to seal. The organ was filled to capacity (>1000 ml) from the syringe in the pylorus.

Refinement of Device Parameters for Intracardiac Applications:

Previous work has shown that the HLAA/PGSU system has sufficient adhesive strength on the epicardium (outer layer of heart muscle) and presented encouraging initial results for intracardiac applications. We demonstrated similar pull-off forces on isolated endocardial tissue. The effects of two factors—patch-to-defect diameter ratio and pressure gradient on burst pressure—were then evaluated in an in vitro set-up. A 5 mm defect was created on a piece of heart tissue, closed with a PGSU/HLAA patch with direct UV light application, and then fixed on a chamber providing pressure control and measurement capabilities. Two cases were investigated; for case 1, the pressure was higher in the chamber, simulating the patch attached to the right ventricle septal wall (in the lower-pressure right ventricle 16); in case 2, the pressure was higher outside the chamber, simulating patch attachment to the left ventricle septal wall (in the higher-pressure left ventricle 18). Three different patch-to-defect diameter ratios were investigated (2.2, 1.75 and 1.4) to represent a range of patch sizes. The highest burst pressures were achieved on the simulated left ventricle wall (case 2) with the largest patch.

Lastly, the force applied by a surgeon was measured to be 2.5N using a mechanical tensile tester. The pull-off performance of the device was evaluated using different pre-load values (1, 3 and 5 N) with the same level and time of light activation to determine sensitivity to loads in this range. Pull-off forces for each pre-load demonstrated relative insensitivity of adhesion force to pre-load at these values.

Proof of Concept of Device Reducing Ventricular Septal Defect (VSD) In Vivo

Device functionality was demonstrated in vivo in a large animal (porcine model, n=3). A VSD was created by guiding the balloon catheter device through the septum into the LV; and the procedure was performed in a beating heart with 2D and 3D echocardiographic monitoring. No intraoperative complications were observed. The procedural steps were successful and the PGSU patch was attached to the septum, confirmed by echo and postmortem gross organ evaluation. Pull-off testing was not carried out for in vivo tissue samples as functional data with echo showing patch attachment to the wall demonstrated that the patch was attached with sufficient adhesion force.

Figure 47:
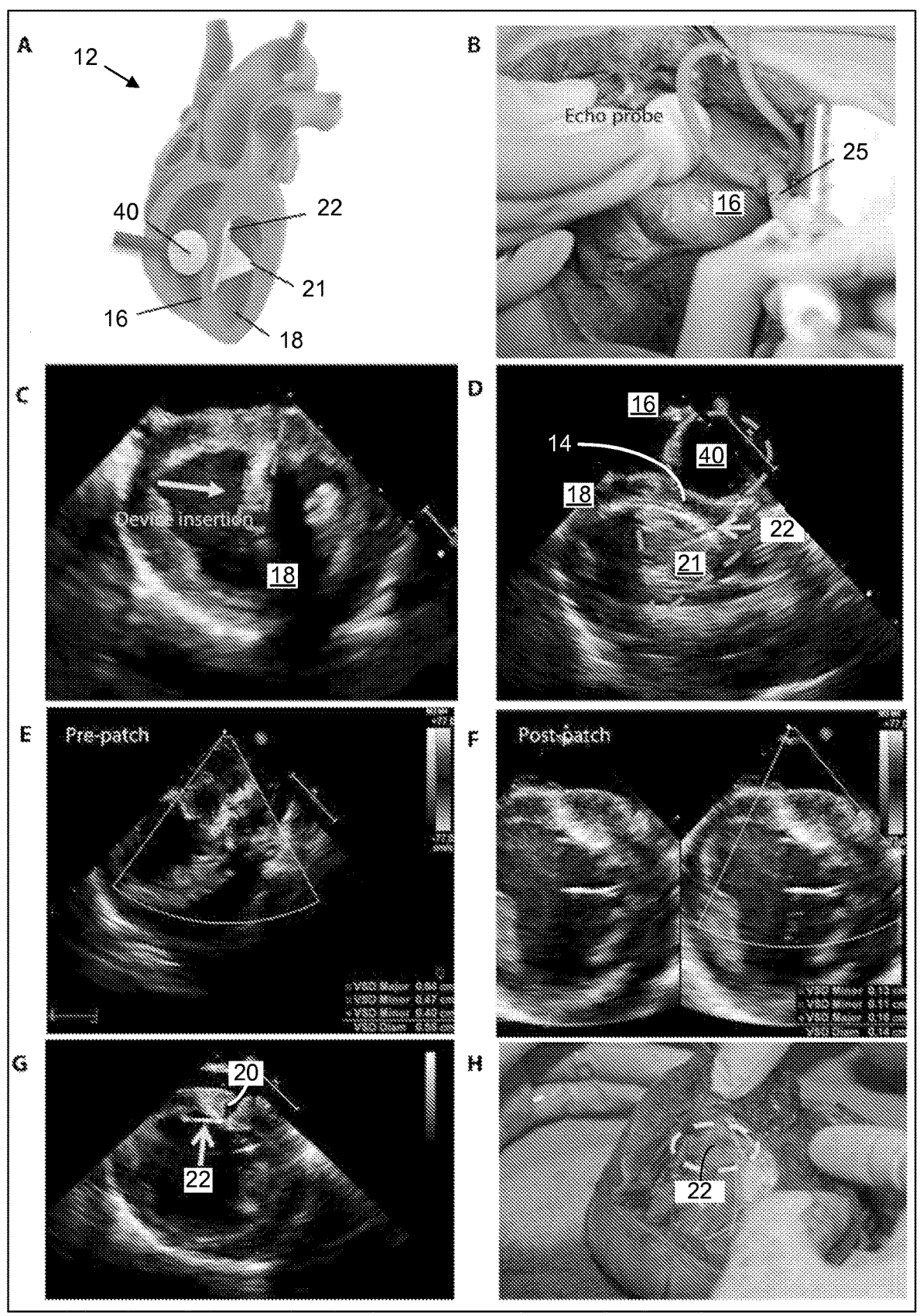
FIG. 47 includes a series of images, including (A) a schematic of the device in a cross section of the heart; (B) access for an in vivo procedure showing anterolateral thoracotomy, position of echo probe and RV access through a purse-string suture; (C)-(G) echocardiograph images throughout a VSD patching procedure; and (H) the patch adhered on the heart following the procedure.

In one case, illustrated in FIG. 47, the VSD was created in a two-step procedure (catheter guidance through the removal, then re-entry into the defect with another device). In this case, a reduction of flow diameter through the defect was observed from a VSD diameter of 5.5 mm to 1.4 mm. Reduction in defect to a size of 1.6 mm with open heart surgery is considered adequate, as residual defects less than 2 mm are reported to spontaneously close within 1 year in humans, A. Dodge-Khatami, et al., "Spontaneous closure of small residual ventricular septal defects after surgical repair," 83 Ann. Thorac. Surg. 902-5 (2007).

In the proof-of-concept illustrations of FIG. 47, (A) a schematic of the device is shown in a cross section of the heart; (B) access is shown for an in vivo procedure showing anterolateral thoracotomy, position of echo probe and RV access through a purse-string suture, which is used to maintain a seal around the device during the procedure; (C) an echocardiograph is presented showing visualization of device insertion into the LV (catheter shaft demarcated by dashed lines); (D) an echocardiograph is presented showing the two inflated balloons (demarcated by dashed lines); (E) an echocardiograph is presented with Doppler flow pre-patch implantation showing an average VSD diameter of 5.5 mm; (F) an echocardiograph is presented with Doppler flow post-patch implantation showing an average VSD diameter of 1.4 mm; (G) an cho of the patch is shown on the septum VSD; (H) the patch is shown adhered on the heart following the procedure.

Additional Applications

In addition to the closure of ventricular septal defects, the technology described herein can be applied/modified for various other uses, including the various exemplary applications that follow.

First, the apparatus and methods can be used for closure of other cardiac defects, such as intracardiac defects; atrial septal defects (ASD); patent foramen ovale (PFO); patent ductus arteriosus (PDA); and defects created by transcatheter procedures, such as trans-apical or trans-septal valve replacements. The patch/adhesive system can be used for closure of the left atrial appendage or for endoventricular cardiac patch plasty [e.g., via the Dor procedure, as described in V. Dor, et al., "Left ventricular reconstruction by endoventricular circular patch plasty repair: a 17-year experience" (2001), for acute left ventricular aneurysm].

With regards to closure of intracardiac defects, an atraumatic device that delivers a biodegradable elastic patch and secures it to the ventricular septal wall with a biodegradable adhesive, as described herein, is advantageous for the following reasons: (i) it can provide atraumatic fixation to the septum that does not rely on mechanical anchorage of the occluder; (ii) an elastic patch/adhesive system prevents tissue erosion and electrical conduction damage; (iii) the tunable biodegradability of the system means that no permanent foreign objects remain in the heart; and (iv) attachment to the septal wall on the left ventricular side is favorable in terms of pressure gradients. A maximum waiting time of two minutes was demonstrated for adhesive activation without the need for angiography, using non-invasive echocardiographic guidance instead (and without the use of any mechanical anchorage—with only the adhesive providing the anchoring).

Second, the apparatus and methods can also be applied to the neck of cranial aneurysms or aortic aneurysms, functioning to effectively seal the aneurysm (or dramatically reduce the neck) from the blood flow in an atraumatic manner, thus preventing rupture. This approach is different from previous approaches in that the patch is cured from inside the defect with reflected light, sealing off the neck.

Third, the apparatus and methods can be used for gastro-intestinal applications (for example, closing duodenal ulcers, stomach (peptic) ulcers, esophageal ulcers and bowel perforations). In these applications, the device can enter through the esophagus and exit through the ulcer. Ulcer perforations can have up to a 30% one-year mortality rate, with intervention-related adverse events being a main contributor to this high rate. Surgical options for large ulcers (>1 mm in diameter) include pyloroplasty and gastrojejunal/gastroduodenal resection and reconstruction. The role of endoscopic procedures for treatment of perforated peptic ulcer in elective and emergency situations has been controversial, largely due to the absence of a device that seals the ulcer. A NOTES procedure to close ulcers is advantageous, as it does not require general anesthesia, similar to placing a percutaneous endoscopic gastrostomy (PEG) tube; but a reliable gastric closure method has been one of the fundamental challenges. Device described herein, specifically with a double patch configuration may provide a viable solution to this challenge.

Fourth, the apparatus and methods can be used for patching hernias, wherein the device is inserted through the abdominal wall, and the patch is adhered to the abdominal wall. For abdominal hernia repair, it is well accepted clinically that the weakened area in the muscle wall can be repaired surgically with sutures after the hernia is pushed back into place (herniorrhaphy); however this technique is typically limited to small hernias with healthy surrounding tissues. Hernioplasty is an alternative technique to repair hernias where synthetic mesh patches are attached over the weakened area, but this approach tends to have longer surgical times and can be associated with negative outcomes. Alternatively, laparoscopic hernioplasty involves mesh patch placement from inside the abdominal wall and attaching the mesh with hernia tacks. This approach can lead to smaller incisions and faster recovery time, but tack placement is still associated with limitations, such as infection and hernia reoccurrence. The use of a device, as described herein, for hernia repair with a patch and biodegradable adhesive can exploit advantages of laparoscopy without using tacks, thereby avoiding the limitations of tacks.

Fifth, the apparatus and methods can be used for urology applications (for example, as a minimally invasive urethral bulking agent or as an intravesical drug delivery system where a bioerodible sustained release patch is placed in the bladder through the urethra, providing sustained release of drugs to the bladder).

Sixth, the apparatus and methods can be used as a directional illuminating catheter to aid with endoscopic procedures and to illuminate difficult-to-see areas. For example, the device can be used at the urethrovesical junction (for benign prostatic hyperplasia detection, for example), in the bronchial tree, or in the gastro-intestinal tract for diagnosis of ulcers, constriction, or Crohn's disease.

Seventh, the apparatus and methods can be used for photodynamic therapy with photosensitizers in the UV range. In photodynamic therapy, photosensitizers accumulate preferentially in malignant tissues, and photoactivation with appropriate wavelength of light can release toxic molecules that lead to tumor tissue death. With this device, the UV wavelengths can be used for this therapy. For example, the photosensitizer porfimer sodium has a peak absorption in the area of 405 nm (blue-violet). Photodynamic therapy is approved by the US Food and Drug Administration (FDA) for endobronchial and esophageal cancers, and is being investigated for skin cancers, ovarian cancer, breast cancers and tumors of the retina. When used for photodynamic therapy, the adhesive can be omitted from the device.

Eighth, in the area of photodynamic therapy, the apparatus and methods can use the reflective coating to achieve spatial control and directional enhancement of illuminated areas, minimizing damage of healthy tissues, which can be useful for treatment of cancers, as mentioned above.

Ninth, the balloon can be used to enhance light delivery for applications, such as crosslinking of vascular tissue, treatment of varicosity, or the delivery of a low-power laser for encouraging stem-cell-based regeneration.

Tenth, the methods and apparatus can be adapted to apply a patch for sustained delivery of cells or drug therapy from a shape memory biomaterial or from a material that requires fixation on tissue.

Eleventh, the patch can act as a self-sealing access port for multiple entries (for example, in transapical procedures).

Twelfth, the light can be focused forward from the catheter (e.g., to activate glue at the distal end of the catheter directly without the need for the internal reflection). Examples of this approach include sticking a patch on the epicardium for infarct reinforcement or drug/patch delivery or for attachment of the outer patch in the second stage of apical closure. This approach can also be used to cure glue on the patch after the procedure if the residual hole/cross in the patch is to be sealed. Additionally, this approach can be beneficial for other applications, such as gastrointestinal applications, urethral applications, left atrial appendage closure, photodynamic therapy, etc. (any instance where the glue is to be activated distal to the catheter).

In still other embodiments, the methods and apparatus can (a) use glue or the patch on the liver to stop hemorrhaging, (b) use the patch for left atrial appendage closure, (c) provide abdominal aneurysm closure, (d) provide reinforcement on infarcted tissue; (e) provide apical closure after transcatheter aortic valve implantation (may need double patch) or any other transapical procedure; (f) deliver urethral or vesical bulking agents; (g) provide a vascular or surgical sealant (e.g., via the application of adhesive); (g) deliver a drug/bioagent releasing therapeutic patch, or (h) patch a defect in the spleen.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references may or may not be included in embodiments of this invention. Still further, the components and steps identified in the Background section are integral to this disclosure and can be used in conjunction with or substituted for components and steps described elsewhere in the disclosure within the scope of the invention. In recitations of the methods in the claims or elsewhere, where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. An insertable light-dispensing catheter device, comprising:
   a plurality of concentrically mounted shafts including:
      (a) an outer shaft for insertion of the device;
      (b) a retractable intermediate shaft inside the outer shaft; and
      (c) an inner shaft inside the retractable intermediate shaft;
   a light guide extending through and deployable from the inner shaft, wherein the light guide includes at least one optical fiber;
   a mirror-coated balloon including a balloon and a mirror coated on the balloon;
   an actuator configured to expand and retract the mirror-coated balloon, wherein the actuator includes a fluid conduit extending through the shafts and coupled with the mirror-coated balloon to enable inflation and retraction of the mirror-coated balloon via injection or withdrawal of a fluid to or from the mirror-coated balloon via the fluid conduit, and wherein the mirror-coated balloon is displaceably retractable into the intermediate shaft and extendable from the intermediate shaft;
   a fluid pump coupled with the fluid conduit to pump the fluid through the conduit;
   a light source coupled with the optical fiber to direct light through the optical fiber; and
   a patch mounted about the fluid conduit and positioned to be displaced by the balloon when the balloon is inflated and to receive the light from the optical fiber,
   wherein the retractable intermediate shaft is configured to deploy the balloon and patch when the intermediate shaft is retracted, and wherein the inner shaft protects the light guide.

2. A method for delivering and curing a photo-curable material to attach a patch onto an internal surface using a minimally invasive catheter device, wherein the minimally invasive catheter device comprises:
   a shaft including a proximal and distal end;
   a light guide extending through the shaft, wherein the light guide includes at least one optical fiber;
   an expandable mirror-coated balloon including a balloon and a mirror coated on the balloon;
   an actuator configured to expand and retract the mirror-coated balloon, wherein the actuator includes a fluid conduit extending through the shaft and coupled with the mirror-coated balloon to enable inflation and retraction of the mirror-coated balloon via injection or withdrawal of a fluid to or from the mirror-coated balloon via the fluid conduit, and wherein the mirror-coated balloon is displaceably retractable into the shaft and extendable from the shaft;
   a fluid pump coupled with the fluid conduit to pump the fluid through the conduit;
   a light source coupled with the optical fiber to direct light through the optical fiber; and
   a patch including a photo-curable material and mounted about the fluid conduit and positioned to be displaced by the balloon when the balloon is inflated and to receive the light from the optical fiber,
   the method comprising:
   penetrating an enclosure with the catheter device, wherein the enclosure contains an internal structure;

displaceably extending the mirror-coated balloon from the shaft into a position wherein the mirror receives and reflects light emitted from shaft into a position where the mirror receives and reflects light emitted from the light guide to the patch;

extending the patch including the photo-curable material from the catheter device inside the enclosure;

placing the patch in contact with internal structure in the enclosure;

directing light through the catheter device to the mirror; and reflecting the light with the mirror onto the photo-curable material of the patch to bond the patch to the internal structure.

3. The method of claim 2, wherein the enclosure is a living organism, and wherein the internal structure is internal tissue of the living organism.

4. The method of claim 2, further comprising:

extending the mirror along with the patch from the catheter device into the enclosure;

directing light through the catheter device to the mirror; and reflecting the light with the mirror onto the photo-curable material of the patch.

5. The method of claim 4, further comprising expanding the mirror-coated balloon inside the living organism, wherein expansion of the mirror-coated balloon places the patch in contact with the internal tissue.

6. The method of claim 5, wherein the expandable mirror-coated balloon includes at least an inner layer and an outer layer, wherein the inner layer inflates and deflates, and wherein the patch is in contact with the outer layer.

7. The method of claim 6, wherein the patch includes a suture that passes through the outer layer, the method further comprising removing the suture to release the patch from the outer layer before reflecting the light onto the photo-curable material.

8. The method of claim 5, further comprising applying a pre-load force onto the patch against the internal tissue via expansion of the mirror-coated balloon, wherein the internal tissue is a ventricular or atrial septum of a human, wherein the ventricular or atrial septum includes a defect that is covered by the patch.

9. The method of claim 5, further comprising:

applying a patterned mask to the mirror-coated balloon; and depositing a coating on the mirror-coated balloon through the mask.

10. An insertable light-dispensing catheter device, comprising:

a shaft including a proximal and distal end;

a light guide extending through the shaft, wherein the light guide includes at least one optical fiber;

an expandable mirror-coated balloon including a balloon and a mirror coated on the balloon;

an actuator configured to expand and retract the mirror-coated balloon, wherein the actuator includes a fluid conduit extending through the shaft and coupled with the mirror-coated balloon to enable inflation and retraction of the mirror-coated balloon via injection or withdrawal of a fluid to or from the mirror-coated balloon via the fluid conduit, and wherein the mirror-coated balloon is displaceably retractable into the shaft and extendable from the shaft;

a fluid pump coupled with the fluid conduit to pump the fluid through the conduit;

a light source coupled with the optical fiber to direct light through the optical fiber; and a patch mounted about the fluid conduit and positioned to be displaced by the mirror-coated balloon when the mirror-coated balloon is inflated and to receive the light from the optical fiber, wherein the mirror-coated balloon is displaceably retractable into the shaft and displaceably extendable from the shaft into a position where the mirror receives and reflects light emitted from the light guide to the patch.

11. The insertable light-dispensing catheter device of claim 10, further comprising a photo-curable adhesive contained in the patch or coated on the patch on a side of the patch opposite the mirror-coated balloon.

12. The insertable light-dispensing catheter device of claim 11, wherein the patch and the photocurable adhesive are biodegradable in a human body.

13. The insertable light-dispensing catheter device of claims 12, wherein the patch comprises an elastomeric material.

14. The insertable light-dispensing catheter device of claim 12, wherein the photo-curable adhesive comprises poly(glycerol sebacate acrylate).

15. The insertable light-dispensing catheter device of claim 14, wherein the patch is substantially optically transparent.

16. The insertable light-dispensing catheter device of claim 10, further comprising a stabilization-and-support balloon extendable from and retractable into the shaft, wherein the stabilization-and-support balloon is mounted with the patch positioned between the stabilization-and-support balloon and the mirror-coated balloon.

17. The insertable light-dispensing catheter device of claim 10, further comprising an outer balloon inside which the mirror-coated balloon is mounted.

18. The insertable light-dispensing catheter device of claim 10, wherein the patch comprises a sensor.

19. The insertable light-dispensing catheter device of claim 10, wherein the patch comprises at least one of a pharmaceutical composition and biological cells.

20. The insertable light-dispensing catheter device of claim 10, wherein the shaft has an outer diameter of less than 8 mm.

21. The insertable light-dispensing catheter device of claim 10, further comprising a poly(p-xylylene) coating on at least one surface of the device.

* * * * *